(12) United States Patent
Pelissier et al.

(10) Patent No.: US 11,804,020 B2
(45) Date of Patent: Oct. 31, 2023

(54) SYSTEMS AND METHODS FOR RENDERING MODELS BASED ON MEDICAL IMAGING DATA

(71) Applicant: Clarius Mobile Health Corp., Vancouver (CA)

(72) Inventors: Laurent Pelissier, North Vancouver (CA); Kris Dickie, Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 36 days.

(21) Appl. No.: 17/553,541

(22) Filed: Dec. 16, 2021

(65) Prior Publication Data

US 2022/0207845 A1 Jun. 30, 2022

Related U.S. Application Data

(60) Provisional application No. 63/131,280, filed on Dec. 28, 2020.

(51) Int. Cl.
| | |
|---|---|
| *G06T 19/20* | (2011.01) |
| *G06T 17/00* | (2006.01) |
| *G06T 7/00* | (2017.01) |
| *G16H 30/20* | (2018.01) |
| *A61B 34/10* | (2016.01) |

(52) U.S. Cl.
CPC ............. *G06T 19/20* (2013.01); *A61B 34/10* (2016.02); *G06T 7/0012* (2013.01); *G06T 17/00* (2013.01); *G16H 30/20* (2018.01); *A61B 2034/105* (2016.02); *G06T 2200/24* (2013.01); *G06T 2207/30004* (2013.01); *G06T 2219/2012* (2013.01)

(58) Field of Classification Search
None
See application file for complete search history.

(56) References Cited

U.S. PATENT DOCUMENTS

| | | |
|---|---|---|
| 9,020,217 B2 | 4/2015 | Amyot et al. |
| 2020/0121391 A1* | 4/2020 | Forstein .............. A61F 2/4644 |
| 2020/0196984 A1 | 6/2020 | Sprung et al. |

(Continued)

*Primary Examiner* — Kee M Tung
*Assistant Examiner* — Jed-Justin Imperial
(74) *Attorney, Agent, or Firm* — Julian Ho; Susan Ben-Oliel

(57) ABSTRACT

A method of creating a 3D model, which is a visual representation of at least one physiological parameter, the method comprises deploying an AI model to execute on a computing device communicably connected to a medical imaging device, said medical imaging device acquiring medical imaging data, wherein the AI model is trained so that when it is deployed, the computing device identifies at least one physiological parameter from medical imaging data; acquiring, at the computing device, new medical imaging data; processing, using the AI model, the new medical imaging data to identify at least one physiological parameter (the "at least one identified physiological parameter"); employing the at least one identified physiological parameter to select a corresponding 3D model; and modifying the corresponding 3D model to alter one or more model parameters therein, to match the at least one identified physiological parameter, thereby customizing the visual appearance of the corresponding 3D model.

20 Claims, 10 Drawing Sheets
(4 of 10 Drawing Sheet(s) Filed in Color)

(56) References Cited

U.S. PATENT DOCUMENTS

| | | |
|---|---|---|
| 2021/0166807 A1* | 6/2021 | Quennesson ......... G16H 10/60 |
| 2021/0196385 A1 | 7/2021 | Shelton, IV et al. |
| 2021/0208567 A1 | 7/2021 | Knoplioch et al. |
| 2021/0287363 A1 | 9/2021 | Bhatia et al. |
| 2022/0117507 A1* | 4/2022 | Van Dam ............ A61B 5/0077 |

\* cited by examiner

SYSTEMS AND METHODS FOR RENDERING MODELS BASED ON MEDICAL IMAGING DATA

CROSS-REFERENCE TO RELATED APPLICATIONS

This application claims the benefit of U.S. Provisional Patent Application No. 63/131,280 entitled "SYSTEMS AND METHODS FOR RENDERING MODELS BASED ON MEDICAL IMAGING DATA" filed on Dec. 28, 2020, which is incorporated by reference it its entirety in this disclosure.

FIELD OF THE INVENTION

The present disclosure relates generally to medical imaging, and in particular, systems and methods for rendering models based on medical imaging data.

BACKGROUND OF THE INVENTION

Medical imaging is a medical procedure that involves generating visual representations of a patient's body in the form of images. Medical imaging can involve different types of imaging modalities, such as x-ray, magnetic resonance imaging (MRI), or ultrasound, for example. Medical images may be used by medical professionals to evaluate the health or condition of the patient. In some cases, medical images can be used to identify various physiological parameters of the patient. For example, cardiac medical images may be used to identify heart wall thickness, valve size, and the like. These physiological parameters may be used by medical professionals to diagnose or treat disease.

Many patients wish to understand their physiological parameters to gain a better understanding of their health status. Although this information may be easily understood by medical professionals, many patients have difficulties doing the same. It can be difficult for patients to make sense of physiological parameters since patients generally do not have the same level of knowledge, experience, and training as medical professionals.

One potential method of explaining physiological parameters to patients is to display the medical image from which the physiological parameter was identified. However, it can be difficult for the patient to visualize the orientation of the medical image and map the physiological parameter to the image. Additionally, it can be computationally intensive to process and render raw medical imaging data in a form that can be displayed to the patient, such as, for example, by the creation of 3D ultrasound images.

In addition to the computation workload, creation of such 3D ultrasound images can be time-consuming and require specific user expertise in data acquisition 2D images and their relative spatial information), followed by 3D ultrasound volume reconstruction (e.g., the generation of 3D ultrasound volume from a series of 2D ultrasound images using interpolation and approximation algorithm). Practically, all of this may not be viable in many clinical settings, in which a care provider simply wishes to simply and easily "visually represent" a medical image to a patient.

There is thus a need for improved systems and methods for medical imaging. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

The patent of application file contains at least one drawing executed in color. Copies of this patent or patent application publication with color drawing(s) will be provided by the Office upon request and payment of the necessary fee.

Non-limiting examples of various embodiments of the present disclosure will next be described in relation to the drawings, in which.

DETAILED DESCRIPTION OF THE INVENTION

A. Glossary

Figure 1:
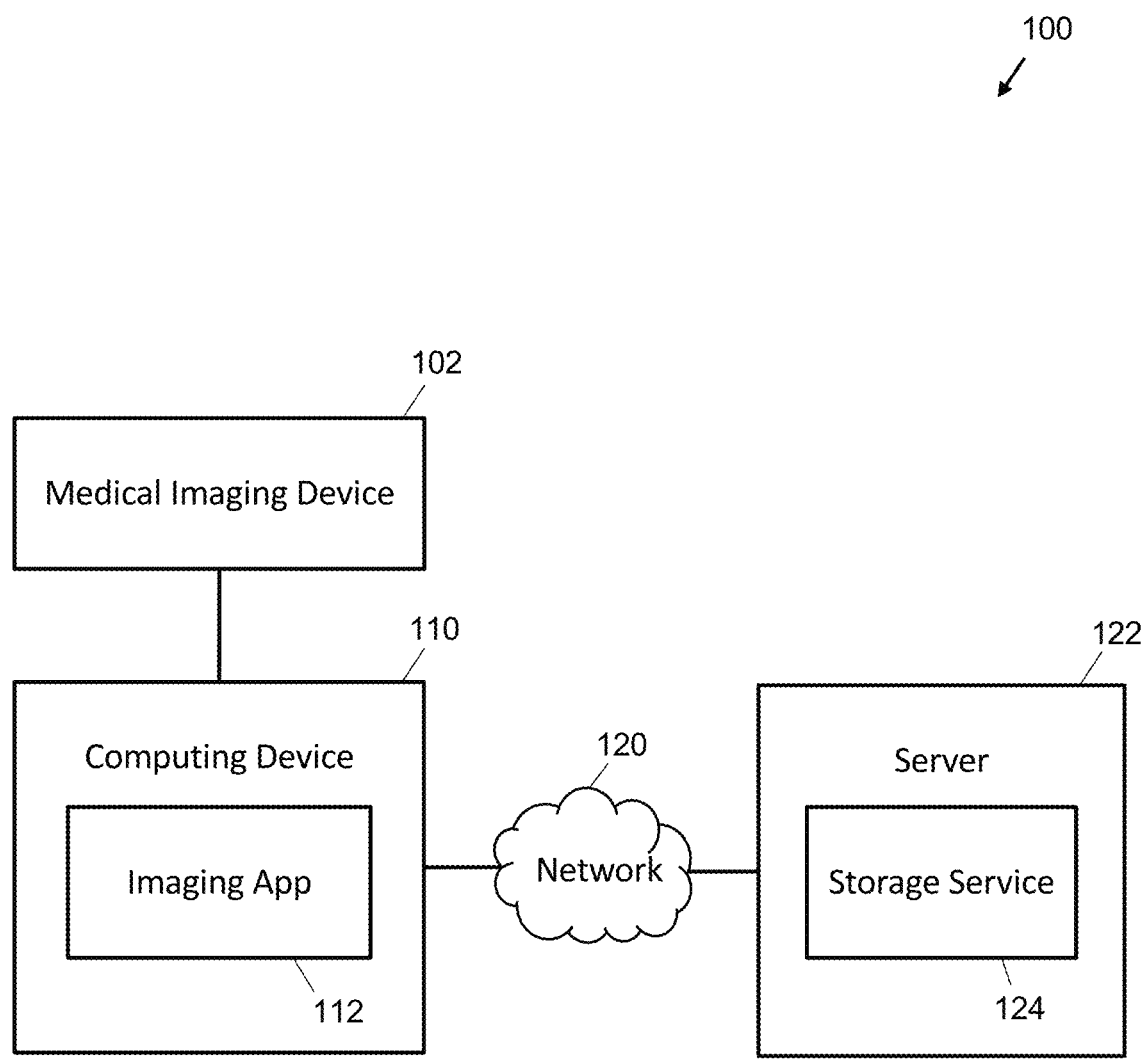
FIG. 1 shows a block diagram of an example medical imaging system, in accordance with at least one embodiment of the present invention.

The term "AI model" means a mathematical or statistical model that may be generated through artificial intelligence techniques such as machine learning and/or deep learning. For example, these techniques may involve inputting labeled or classified data into a neural network (e.g., a deep neural network) algorithm for training, so as to generate a model that can make predictions or decisions on new data without being explicitly programmed to do so. Different software tools (e.g., TensorFlow™, PyTorch™, Keras™) may be used to perform machine learning processes.

The term "module" can refer to any component in this invention and to any or all of the features of the invention without limitation. A module may be a software, firmware or hardware module, and may be located, for example, in the medical imaging device (such as an ultrasound scanner), a display device or a server.

The term "rendering engine" can refer to software that draws, manipulates, alters or re-arranges text and images on a screen. More specifically, a rendering engine may reproduce an image based on stored three-dimensional data taking raw information from a 3D image (ex: polygons, materials, textures and lighting) and calculating a final result, which is known as "output". A rendering engine can simulate realistic lighting, shadows, atmosphere, color, texture and optical effects such as light refraction or blur seen on moving objects. Within the scope of the present invention, the output of the rendering engine is the customized 3D model.

The term "communications network" can include both a mobile network and data network without limiting the term's meaning, and includes the use of wireless (e.g. 2G, 3G, 4G, 5G, WiFi™, WiMAX™, Wireless USB (Universal Serial Bus), Zigbee™, Bluetooth™ and satellite), and/or hard wired connections such as local, internet, ADSL (Asymmetrical Digital Subscriber Line), DSL (Digital Subscriber Line), cable modem, T1, T3, fiber-optic, dial-up modem, television cable, and may include connections to flash memory data cards and/or USB memory sticks where appropriate. A communications network could also mean dedicated connections between computing devices and electronic components, such as buses for intra-chip communications.

The term "operator" (or "user") may refer to the person that is operating a medical imaging device (e.g., a clinician, medical personnel, a technician, a radiographer, a sonographer, ultrasound/radiograph/MRI student, a patient, an ultrasonographer and/or ultrasound technician).

The term "medical imaging device" can refer to an ultrasound scanner, an x-ray imager, and a magnetic resonance imaging (MRI) imager.

The term "medical imaging data" can refer to medical images or data associated with the medical images, as created using a medical imaging device.

The term "model parameters" can refer to the size, position, orientation, shape, colour, shading, contrast, and texture of one or more portions of a selected 3D model.

The term "physiological parameter" can refer to one or more physical characteristics (for example, size, shape, orientation) of an anatomical feature, a presence or absence of an anatomical feature, in whole or part, and one or more anomalies in an anatomical feature. These physiological parameters may be used by medical professionals to diagnose, assess progression of and/or treat disease.

The term "3D model" can refer to a photorealistic rendering, generally defined by a plurality of points, comprising one or more model parameters, the latter of which are alterable within the scope of the invention.

The term "processor" can refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). A processor may perform the steps in the flowcharts and sequence diagrams, whether they are explicitly described as being executed by the processor or whether the execution thereby is implicit due to the steps being described as performed by the system, a device, code or a module. The processor, if comprised of multiple processors, may be located together or geographically separate from each other. The term includes virtual processors and machine instances as used in cloud computing or local virtualization, which are ultimately grounded in physical processors.

The term "scan convert", "scan conversion", or any of its grammatical forms refers to the construction of an ultrasound media, such as a still image or a video, from lines of ultrasound scan data representing echoes of ultrasound signals. Scan conversion may involve converting beams and/or vectors of acoustic scan data which are in polar (R-theta) coordinates to cartesian (X-Y) coordinates.

The term "system" when used herein, and not otherwise qualified, refers to a system for creating a 3D model, which is a visual representation of at least one physiological parameter, and, in live deployment, employing an AI model to identify at least one physiological parameter from medical imaging data, employing the identified physiological parameter to select a corresponding 3D model, employing a computer processor to modify the corresponding 3D model to alter one or more model parameters therein, thereby customizing the visual appearance of the corresponding 3D model, forming a customized 3D model, the system being a subject of the present invention. In various embodiments, the system may include a medical imaging device for capturing medical imaging data, (including in some cases a display), one or more computer processors communicatively connected to the medical imaging device; one or more servers which may store a plurality of 3D models, and one or more user interfaces on computing devices.

The term "ultrasound image frame" (or "image frame" or "ultrasound frame") refers to a frame of post-scan conversion data that is suitable for rendering an ultrasound image on a screen or other display device.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

B. Exemplary Embodiments

At a high level, the embodiments herein generally allow for the provision of systems and methods for a specially trained AI model, for use with an imaging app and/or rendering engine that creates a customized 3D model of a physiological parameter identified in a medical image, obtained from a medical imaging device, and systems and methods providing a photo-realistic, visual representation of such a physiological parameter to display to a patient and to assist in the understanding of a diagnosis and treatment options.

In one aspect, the present invention provides a method of creating a 3D model, which is a visual representation of at least one physiological parameter, the method comprising deploying an AI model to execute on a computing device communicably connected to a medical imaging device, said medical imaging device acquiring medical imaging data, wherein the AI model is trained so that when it is deployed, the computing device identifies at least one physiological parameter from medical imaging data; acquiring, at the computing device, new medical imaging data; processing, using the AI model, the new medical imaging data to identify at least one physiological parameter (the "identified physiological parameter"); employing the identified physiological parameter to select a corresponding 3D model; modifying the corresponding 3D model to alter one or more model parameters therein, thereby customizing the visual appearance of the corresponding 3D model.

In another aspect, the present invention provides a system for creating a 3D model, which is a visual representation of at least one physiological parameter, said system comprising a medical imaging device configured to acquire new medical imaging data; a computer processor that is communicatively connected to the medical imaging device and configured to: process the new medical imaging data against an artificial intelligence ("AI") model, wherein said AI model is trained so that when it is deployed, the computer processor identifies at least one physiological parameter from medical imaging data; process, using the AI model, the new medical imaging data to identify at least one physiological parameter (the "identified physiological parameter"); employ the identified physiological parameter to select a corresponding 3D model; modify the corresponding 3D model to alter one or more model parameters therein, thereby customizing the visual appearance of the corresponding 3D model (the customized 3D model); and a display device configured to display to a system user at least the customized 3D model.

In another aspect, the present invention provides a computer-readable media storing computer-readable instructions, which, when executed by a processor cause the processor to process new medical imaging data against an artificial intelligence ("AI") model, wherein said AI model is trained so that when it is deployed, the computer processor identifies at least one physiological parameter from the new medical imaging data (the "identified physiological parameter"); to employ the identified physiological parameter to select a corresponding 3D model; and to modify the corresponding 3D model to alter one or more model parameters therein, thereby customizing the visual appearance of the corresponding 3D model (the customized 3D model).

In yet another aspect, the present invention provides a computing device comprising at least one processor and at least one memory storing instructions for execution by the at least one processor, wherein when executed, the instructions cause the at least one processor: to process new medical imaging data against an artificial intelligence ("AI") model, wherein said AI model is trained so that when it is deployed, the computer processor identifies at least one physiological parameter from the new medical imaging data (the "identified physiological parameter"); to employ the identified physiological parameter to select a corresponding 3D model; and to modify the corresponding 3D model to alter one or more model parameters therein, thereby customizing the visual appearance of the corresponding 3D model (the customized 3D model).

In yet another aspect, the present invention provides a user interface communicatively connected to a computing device which enables manipulation of a corresponding 3D model to alter one or more model parameters therein, thereby customizing the visual appearance of the corresponding 3D model (the customized 3D model).

Referring to FIG. 1, shown there generally as 100 is a block diagram of an example system for rendering models based on medical imaging data, in accordance with at least one embodiment of the present invention. The medical imaging system 100 may include a medical imaging device 102, a computing device 110, and a server 122. Each of the components of the medical imaging system 100 may be connected by a computer network 120 (e.g., the Internet) to facilitate electronic communication. Each of the components of the medical imaging system 100 may be distributed over a wide geographic area.

The medical imaging device 102 may be configured to generate medical imaging data, such as medical images or data associated with the medical images. The medical imaging device 102 may be operated by a medical professional or a patient during a medical imaging examination to generate medical imaging data associated with the patient. The medical imaging device 102 may be an x-ray imager, ultrasound imager (e.g., that transmits and receives ultrasound energy for generating ultrasound images), magnetic resonance imaging (MRI) imager, for example. In some embodiments, the medical imaging device 102 may be communicatively coupled to the computing device 110. For example, the medical imaging device 102 may transmit medical imaging data to the computing device 110 for display thereon. The computing device 110 may then transmit the medical imaging data to the server 122 for storage. In other embodiments, the medical imaging device 102 may directly transmit the medical imaging data to the server 122 for storage.

The medical imaging device 102 may include various components (not shown) for storing software and/or firmware instructions, configuration settings (e.g., sequence tables), and/or medical imaging data. The medical imaging device 102 may also include one or more processors (shown at 132 in FIG. 10) for executing the instructions for performing acts of the methods discussed herein. The medical imaging device 102 may also include various components such as antennas (not shown) for facilitating electronic communication with other devices, such as the computing device 110. The medical imaging device 102 may communicate with other devices directly, and/or through the computer network 120 (also shown by way of example as 210, in FIG. 11).

In some embodiments, the medical imaging device 102 may be an ultrasound scanner. Although the exemplary figures herein refer to the medical imaging device being an ultrasound scanner, the invention is not intended to be limited as such. The ultrasound scanner may be configured to transmit ultrasound energy to a target object, receive ultrasound energy reflected from the target object, and generate ultrasound image data based on the reflected ultrasound energy. The ultrasound scanner may include a transducer which converts electric current into ultrasound energy and vice versa. The transducer may transmit ultrasound energy to the target object which echoes off the tissue. The echoes may be detected by a sensor in transducer and relayed through suitable electronics. In some embodiments, the ultrasound scanner may be provided as a handheld ultrasound probe that transmits the ultrasound image data to the computing device 110 (as shown in FIG. 1) for display thereon.

The computing device 110 may be a multi-use electronic display device such as a smartphone, tablet computer, laptop computer, desktop computer, or other suitable display device. In various embodiments, the computing device 110 may be provided with an input component capable of receiving user input and an output component, such as a display screen, capable of displaying various data. For example, the input component of computing device 110 may include a touch interface layered on top of the display screen of the output component. Computing devices 110 may also include memory, Random Access Memory (RAM), Read Only Memory (ROM), and persistent storage device, which may all be connected to a bus to allow for communication therebetween and with one or more processors. Any number of these memory elements may store software and/or firmware that may be accessed and executed by the one or more processors to perform the methods and/or display the images or models described herein. The computing device 110 may also include various components for facilitating electronic communication with other devices, such as the medical imaging device 102 and/or the server 122.

In the illustrated embodiment, the computing device 110 may be operated by a medical professional or a patient directly to control the operation of the medical imaging device 102. For example, certain input received at the computing device 110 may be relayed to medical imaging device 102 to control the operation of the medical imaging device 102. The computing device 110 may also display medical imaging data (e.g., acquired by medical imaging device 102 or the computing device 110) to the medical professional or the patient. For example, the computing device 110 may retrieve medical imaging data from the medical imaging device 102 and/or the server 122 for display. In some embodiments, the computing device 110 may also transmit medical imaging data retrieved from the medical imaging device 102 or acquired by the computing device 110 itself to the server 122 for storage. In various embodiments, the computing device 110 can generate and display three-dimensional (3D) models based on the medical imaging data.

In various embodiments, the computing device 110 may execute an application that is configured to communicate with the medical imaging device 102 and/or the server 122. In FIG. 1, this is shown as imaging application or "Imaging App" 112. For example, in embodiments where computing device 110 provides a native software distribution platform (e.g., such as the Apple™ App Store™ for iOS™ devices or the Google™ Play Store™ for Android™ devices), the imaging app 112 may be downloaded therefrom. The imaging app 112 may be configured to perform various acts of the methods described herein (e.g., to display three-dimensional models that correspond to medical imaging data acquired by medical imaging device 102).

Referring still to FIG. 1, the server 122 may be configured to provide a storage service 124 to perform various acts discussed herein as being performed by the server 122. The server 122 may be accessible at a first network location (e.g., at a URL and/or at a given Internet Protocol (IP) address). In various embodiments, the storage service 124 may be provided in the form of software instructions configured to execute on server 122. For example, the software instructions may provide an Application Programming Interface (API) that the computing device 110 is configured to access. The server 122 may include various components, such as a processor and memory, for storing and executing the software instructions. Although illustrated as a single server in FIG. 1, the term "server" herein may encompass one or more servers such as may be provided by a suitable hosted storage and/or cloud computing service. In some embodiments, the server 122 may be provided by two or more servers distributed over a wide geographic area.

The server 122 may be configured to store various data using one or more data storages. The data may be stored in the form of a relational database, object-oriented database, and/or any other suitable type of database. The data storage(s) may be local to the server 122 and/or geographically remote to the server 122 and connected via a network. In various embodiments the data stored by the server 122 may be encrypted, hashed, or otherwise secured.

In the illustrated embodiment, the server 122 may store medical imaging data acquired by the medical imaging device 102 or the computing device 110. For example, the medical imaging data may include images captured by the medical imaging device 102 and/or underlying raw data or metadata associated with the images. The server 122 may provide access to the stored medical imaging data to computing device 110. In some cases, the server 122 may restrict access to certain medical imaging data to the computing device 110 for security purposes.

Figure 11:
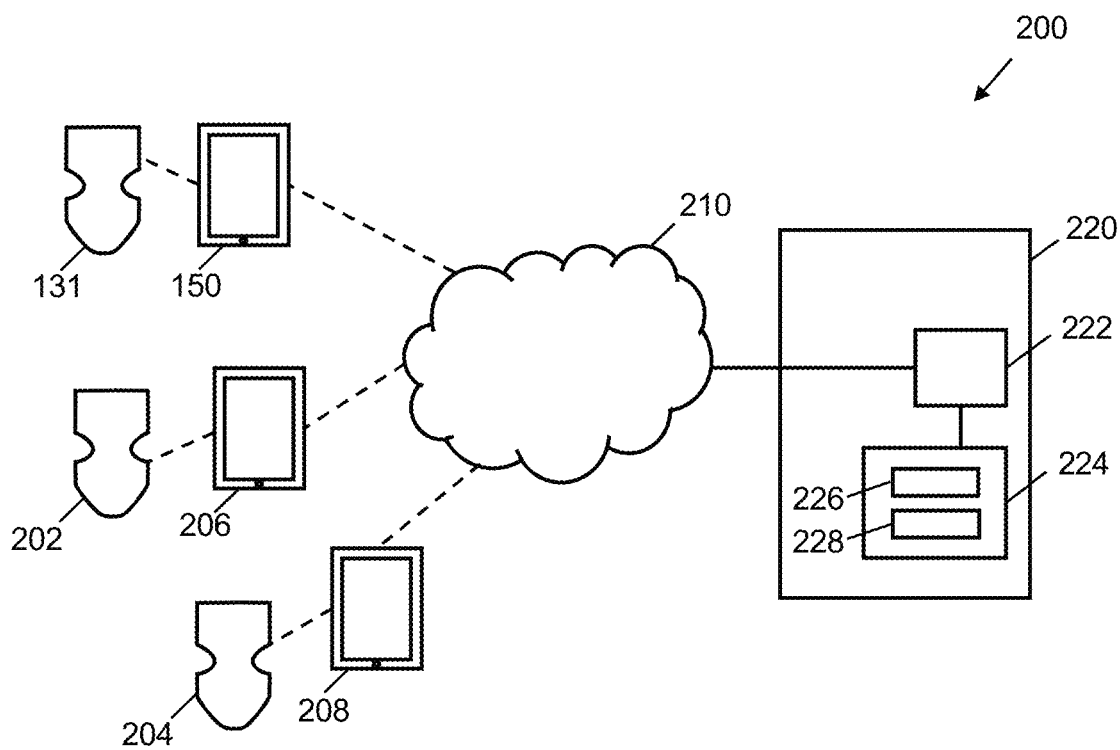
FIG. 11 is a schematic diagram of a system with multiple ultrasound scanners, according to an embodiment of the present invention.

As will be understood by persons skilled in the art, the architecture in FIG. 1 is provided in simplified form for illustration only. Other configurations may be possible in other embodiments. For example, although only one medical imaging device 102, computing device 110, computer network 120, and server 122 is shown in FIG. 1 for ease of illustration, it should be appreciated that the medical imaging system 100 may include any number of these components—for example, as shown in FIG. 11.

Figure 2:
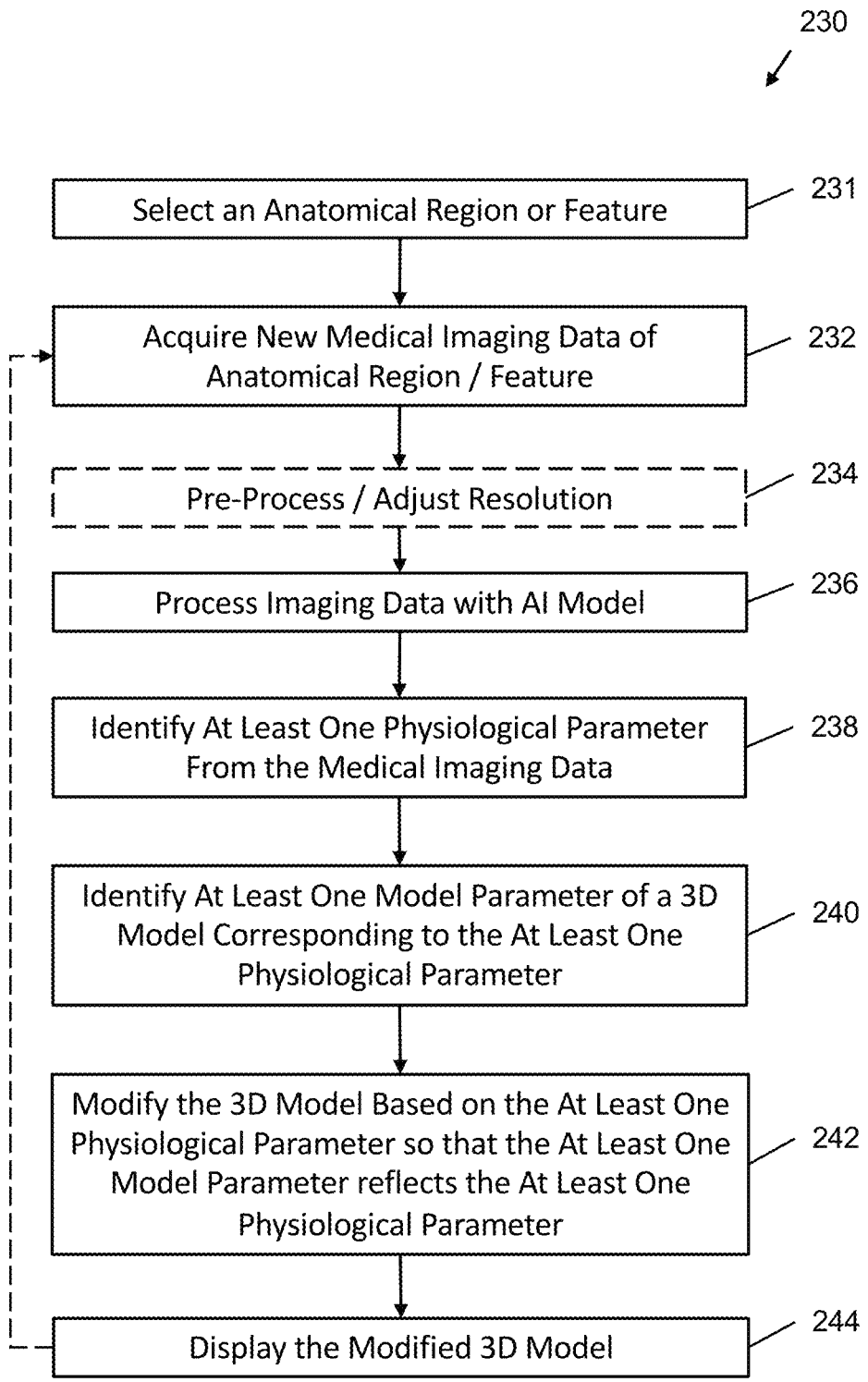
FIG. 2 is a flowchart diagram of an example method of operating the medical imaging system shown in FIG. 1, in accordance with at least one embodiment of the present invention.

Referring to FIG. 2, shown there generally as 230 is a flowchart diagram illustrating an example method of operating the medical imaging system 100, in accordance with at least one embodiment of the present invention. The method 230 may be used to render models (e.g., 3D models) based on medical imaging data. For ease of illustration, FIG. 2 will be described with reference to FIGS. 3A, 3B, 4A, 4B, 5A, and 5B, which show example medical imaging data and the respective three-dimensional models that may be created and displayed by the computing device 110, in accordance with at least one embodiment of the present invention. In discussing the method of FIG. 2, reference will also be made to the various components of the system of FIG. 1 discussed above.

Figure 3A:
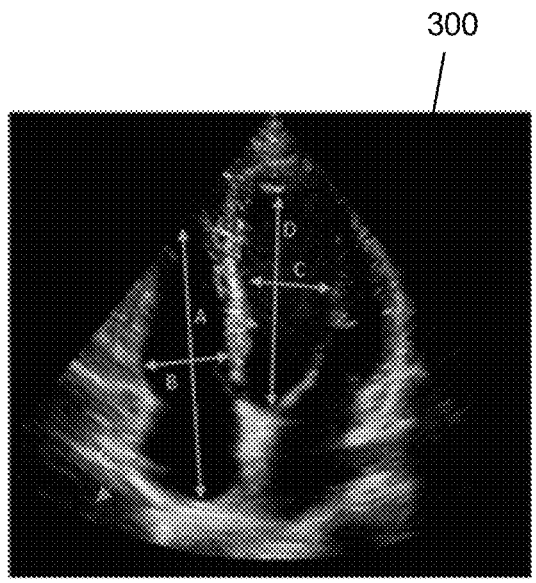
FIG. 3A is an example medical image that can be acquired by the medical imaging system shown in FIG. 1, in accordance with at least one embodiment of the present invention.
Figure 3B:
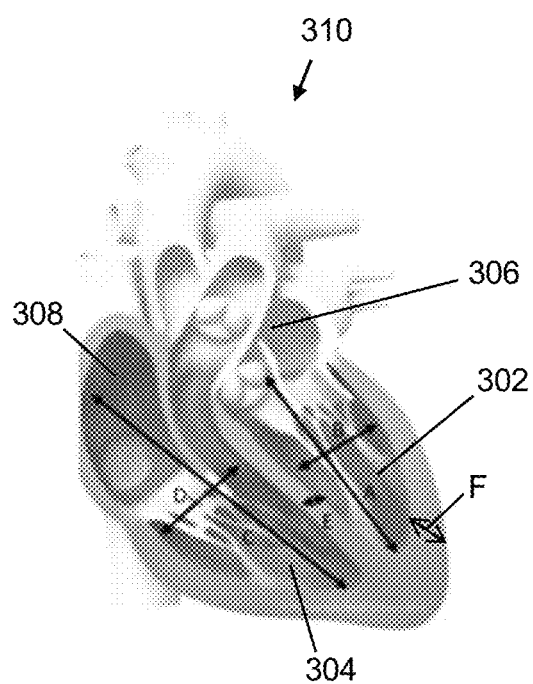
FIG. 3B is an example model that can be generated by the medical imaging system shown in FIG. 1, in accordance with at least one embodiment of the present invention.

At 231, as a first general step, an anatomical region or anatomical feature is selected by a user. For example, as shown in FIGS. 3A and 3B, the region may be related to cardiac operations or otherwise related to the heart. In FIGS. 4A, 4B, 5A and 5B the region may be related to pulmonary operations or otherwise related to the lungs. However, this invention is not intended to be limited to any specific anatomical region or anatomical feature, and the methods and systems may be considered highly useful for regions or features in which dimensions (size, depth, shape, etc . . . ), and/or textural changes are measurable and possibly indicative of medical changes, concerns or issues. For example, anatomical regions for which 3D models may be useful include, but are not limited to cardiac, thoracic and hepatic regions.

Liver elastography is a type of imaging test that checks the liver conditions such as fibrosis, which is a condition that reduces blood flow to and inside the liver causing the buildup of scar tissue. Left undetected and untreated, fibrosis can lead to cirrhosis, liver cancer, and liver failure. Within the scope of the invention, a 3D model may be created which is indicative of the degree of fibrosis in a liver with one/ore model parameters of a selected 3D model being manipulated to match one or more physiological parameters, the latter being the degree and location of detected fibrosis determined based on various elastography methods. For example, ultrasound elastography can use sound waves to measure the stiffness of liver tissue. Additionally or alternatively, MRE (magnetic resonance elastography), can combine ultrasound technology with magnetic resonance imaging (MRI) to detect fibrosis. In an MRE test, a computer program may create a visual map that shows liver stiffness that may be used as the physiological parameter discussed herein.

Figure 4A:
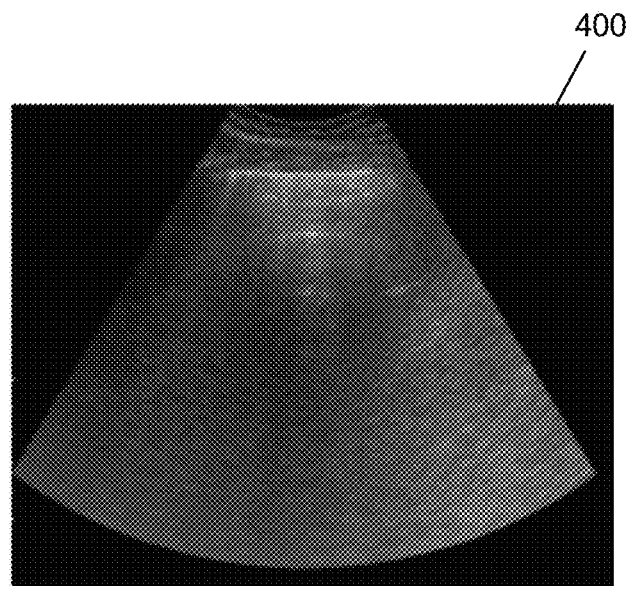
FIG. 4A is another example medical image that can be acquired by the medical imaging system shown in FIG. 1, in accordance with at least one embodiment of the present invention.
Figure 5A:
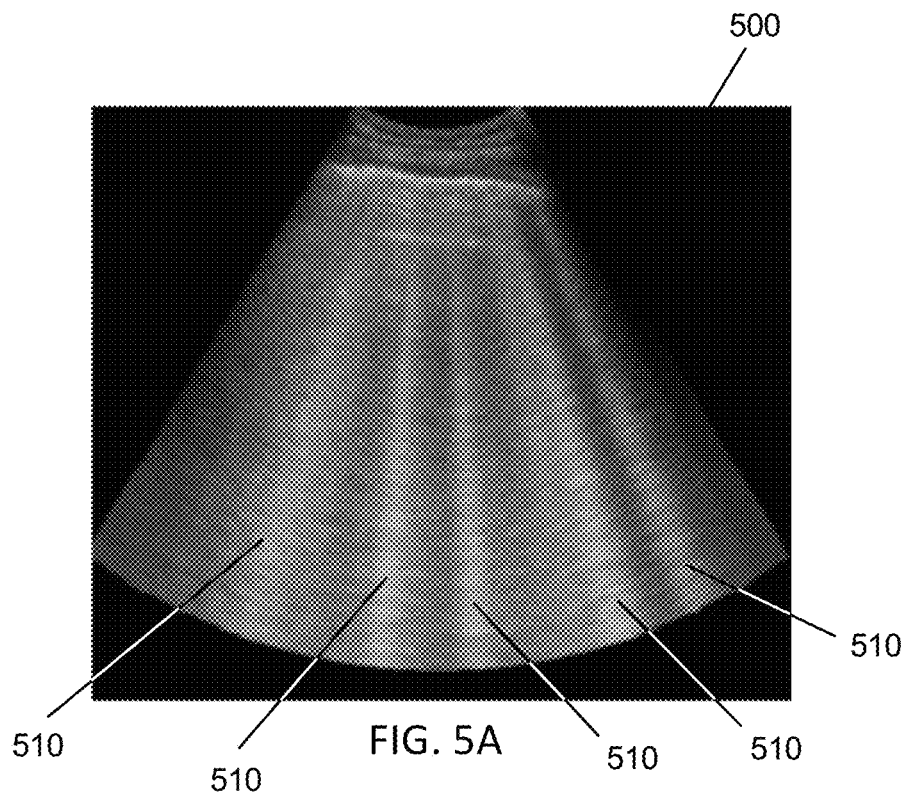
FIG. 5A is another example medical image that can be acquired by the medical imaging system shown in FIG. 1, in accordance with at least one embodiment of the present invention.

At 232, the medical imaging system 100 may acquire new medical imaging data. For example, a medical professional or patient may operate the computing device 110 and/or the medical imaging device 102 to capture images of the patient. In an example embodiment where the medical imaging device 102 is an ultrasound scanner that acquires ultrasound images for display on computing device 110, the medical imaging data may be ultrasound image data. For example, FIGS. 3A, 4A, and 5A show example ultrasound images (300, 400 and 500, respectively) that can be acquired by the medical imaging system 100 at act 232. More specifically, FIG. 3A at 300 shows an example cardiac ultrasound image and FIG. 4A at 400 and 5A at 500 show example lung ultrasound images.

Although FIGS. 3A, 4A, and 5A illustrate post-scan converted ultrasound data, it should be appreciated that the new medical imaging data may include raw or unprocessed data that cannot be directly displayed as an image. For example, in the case of ultrasound imaging data, the medical imaging data may include radio frequency (RF) data, pre-scan converted data, and/or post-scan converted data. The term "scan conversion", as noted above, refers to construction of ultrasound media, such as a still image or a video, from lines of ultrasound scan data representing echoes of ultrasound signals. Scan conversion may involve converting beams and/or vectors of acoustic scan data which are in polar (R-theta) coordinates to cartesian (X-Y) coordinates.

In some embodiments, an optional pre-processing act 234 may be performed on the new medical imaging data. For example, if the medical imaging data is ultrasound image frames, these steps may facilitate improved performance and/or accuracy when processing through the machine learning (ML) algorithm. For example, it may be possible to pre-process ultrasound images through a high contrast filter to reduce the granularity of greyscale on the ultrasound images.

Additionally, or alternatively, it may be possible to reduce the scale of the ultrasound images prior to providing the ultrasound images to the processing against the AI model step 236. Reducing the scale of ultrasound images as a preprocessing step may reduce the amount of image data to be processed and thus may reduce the corresponding computing resources required for the processing act 236 and/or improve the speed of the processing act 236.

Various additional or alternative pre-processing acts may be performed in act 234. For example, these acts may include data normalization to ensure that the various ultrasound frames used for training have generally the same dimensions and parameters.

Figure 10:
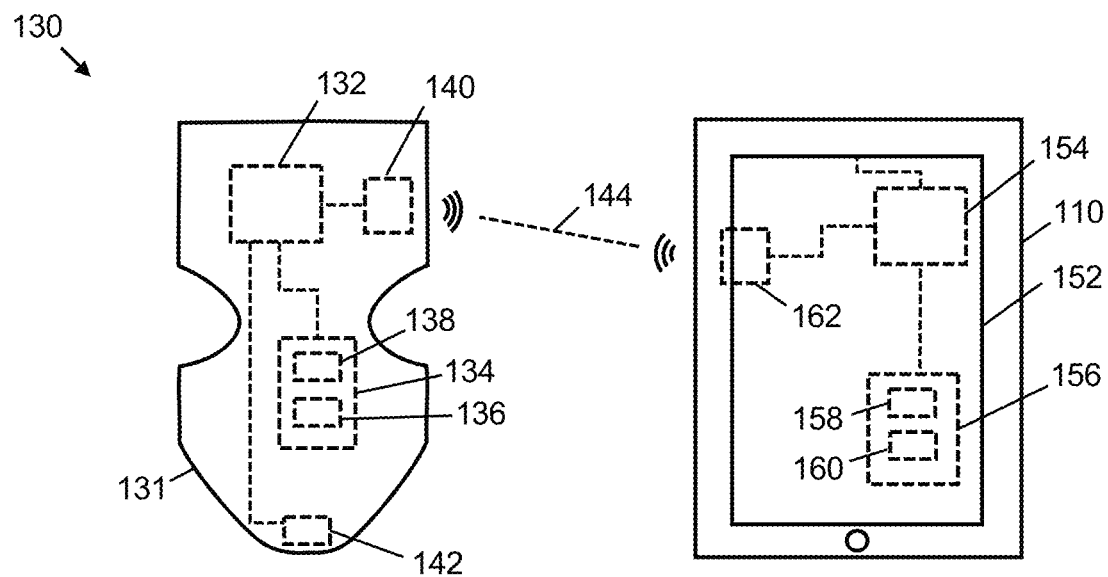
FIG. 10 is a schematic diagram of an ultrasound imaging system, according to an embodiment of the present invention.

In various embodiments, the new medical imaging data acquired at act 232 may be live images acquired by an ultrasound imaging system (e.g., the system discussed with respect to FIGS. 1, 10 and 11). For example, the AI model may be deployed for execution on the scanner 131 and/or the display device 150 discussed in more detail below. Additionally, or alternatively, the AI model may be executed on stored images that were previously acquired (e.g., as may be stored on a Picturing Archiving and Communication System (PACS)).

Figure 7:
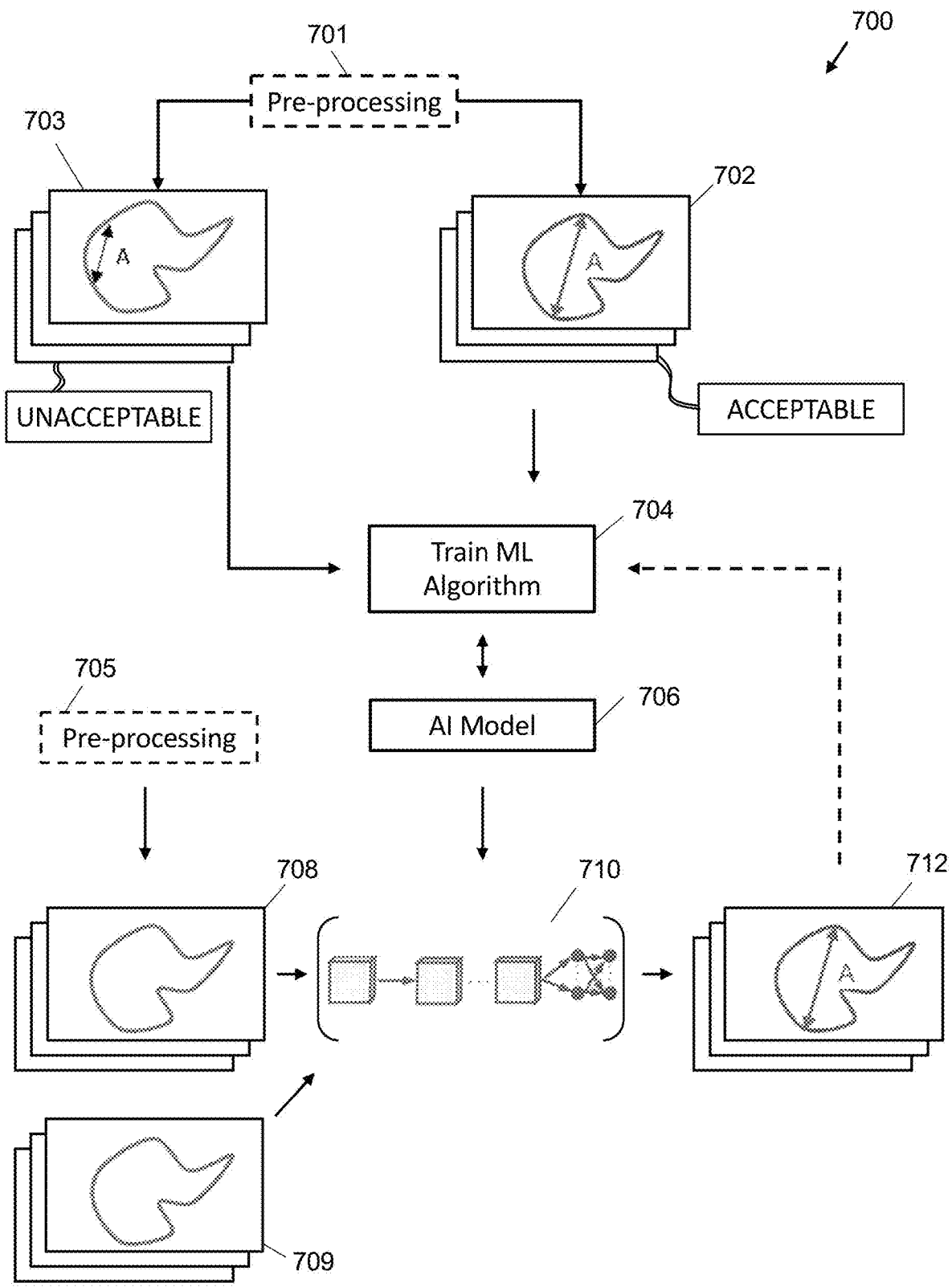
FIG. 7 is a schematic diagram of the training and deployment of an AI model, according to an embodiment of the present invention.
Figure 8:
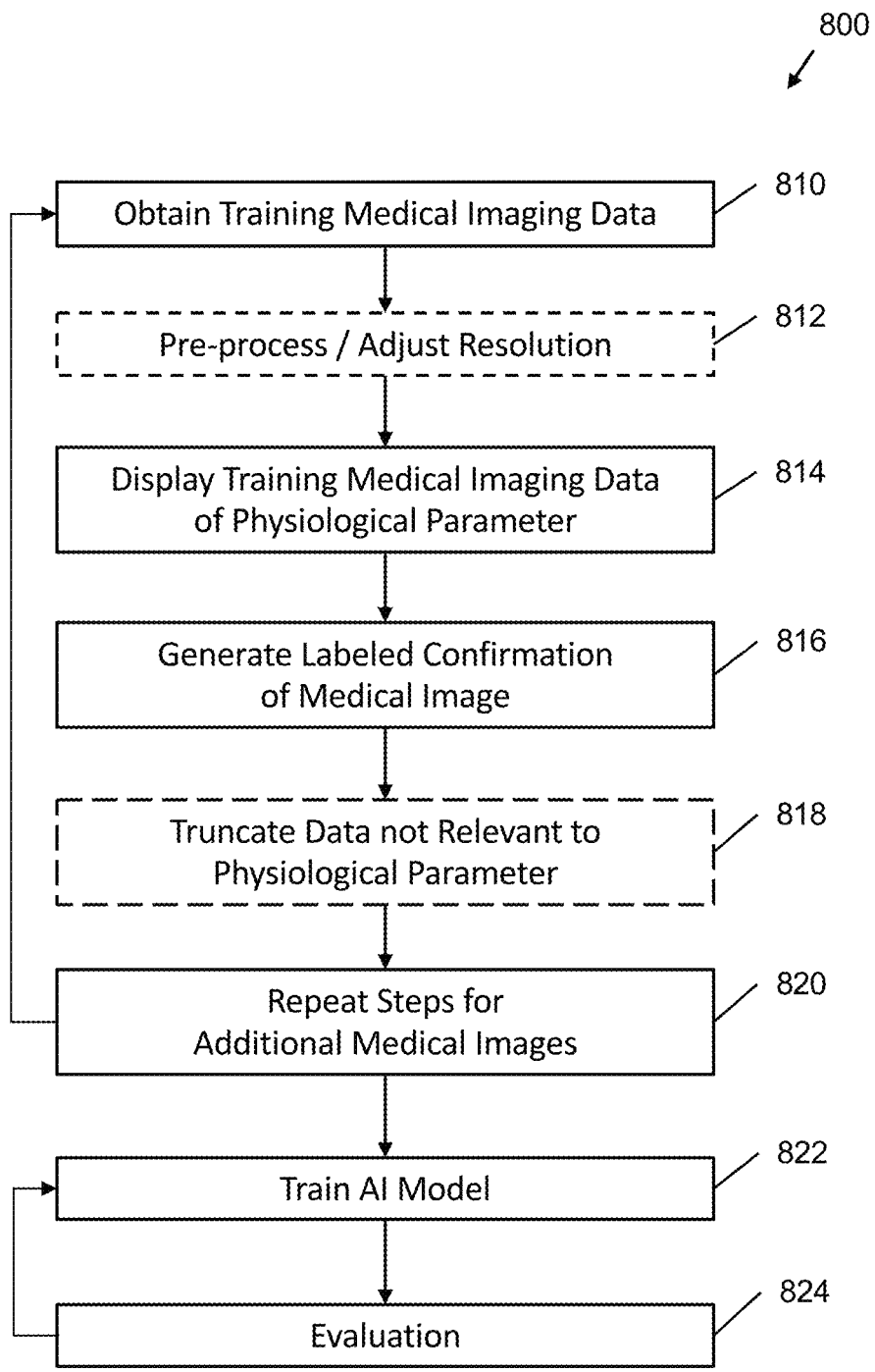
FIG. 8 is a flowchart diagram of an example method for training an artificial intelligence model that can be used when operating the medical imaging system shown in FIG. 1, in accordance with at least one embodiment of the present invention.

At act 236, new medical imaging data acquired at act 232 is processed through a trained AI model (the creation and training of which is described in further detail in FIGS. 7 and 8). At act 238, the medical imaging system 100 can identify at least one physiological parameter from the medical imaging data using an artificial intelligence (AI) model. As noted above, the AI model is a mathematical or statistical model that may be generated through artificial intelligence techniques such as machine learning and/or deep learning. For example, these techniques may involve inputting labeled or classified data into a neural network algorithm for training, so as to generate a model that can make predictions or decisions on new data without being explicitly programmed to do so. Different software tools (e.g., TensorFlow™, PyTorch™, Keras™) may be used to perform machine learning processes. The generation of an AI model will be described in more detail below with regard to FIG. 7 and FIG. 8.

Various physiological parameters can be identified by the medical imaging system 100 at act 238, depending on the type of medical imaging data acquired. In some cases, the physiological parameters may depend on the type of anatomy imaged. For example, the physiological parameters identified for a set of cardiac ultrasound imaging data may differ from the physiological parameters identified for a set of lung ultrasound imaging data which in turn may differ for physiological parameters identified for hepatic tissue imaging data. The physiological parameters may also depend on the orientation of the medical imaging data.

Figure 6:
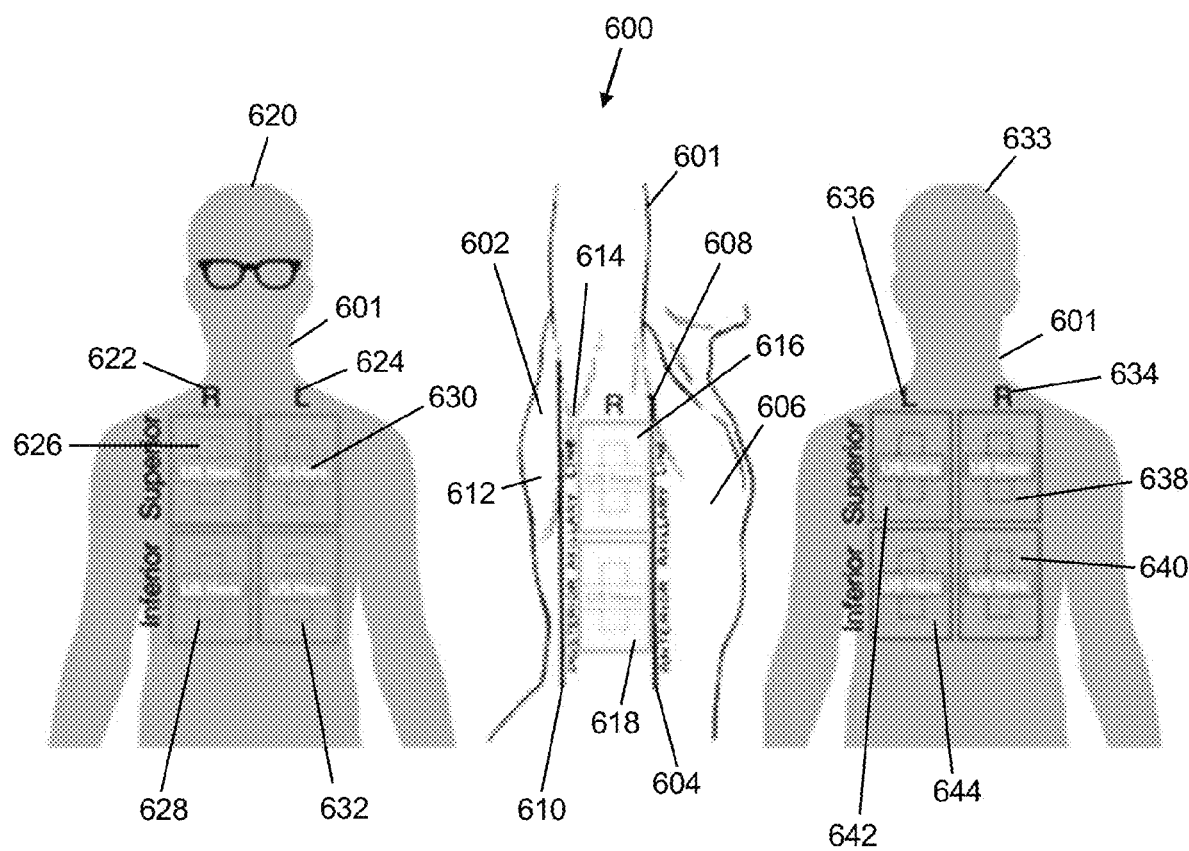
FIG. 6 is an anatomical diagram illustrating a protocol for example locations on a human body that can be imaged using the medical imaging system shown in FIG. 1.

For example, FIG. 6, generally at 600, illustrates twelve different imaging locations within the thorax, from which ultrasound imaging data may acquired in order to acquire and identify physiological parameters at varying orientations. Each imaging location will result in medical imaging data having a different orientation. Different physiological parameters may be identified, depending on the imaging location. More specifically, patient view 602 of patient 601, illustrates anterior axillary line 604, which is a coronal line on anterior torso 606 marked by anterior axillary fold 608. It is an imaginary line that runs down from the point midway between the middle of the clavicle and the lateral end of the clavicle. Further, patient view 602 illustrates posterior axillary line 610 is a coronal line on posterior torso 612 marked by posterior axillary fold 614. Between anterior axillary line 604 and posterior axillary line 610, there is shown two right side imaging locations (616 and 618). A similar two imaging locations may be available on the left side of the patient view (not shown), due to such images being mirror to those on the right side (shown).

Still referring to FIG. 6, patient view 620 of patient 601 illustrates a front right (622) and front left (624) orientation of the thorax. Front right 622 is divided into superior thorax region 626 and inferior thorax region 628. Front left 624 is divided into superior thorax region 630 and inferior thorax region 632. Similarly, patient view 633 of patient 601 illustrates a back right (634) and back left (636) orientation of the thorax. Back right 634 is divided into superior thorax region 638 and inferior thorax region 640. Back left 636 is divided into superior thorax region 642 and inferior thorax region 644.

In some embodiments, the AI model may identify the type of anatomy imaged (e.g., the type of organ or tissue imaged) and/or the particular cross-sectional view of tissue/organ imaged and/or the orientation of the tissue/organ imaged, when determining the physiological parameters to be identified. For example, the AI model may be able to determine that certain acquired medical imaging data corresponds to a particular cross-sectional view of the heart (e.g., a 4-chamber apical view and/or a 2-chamber parasternal view).

In some embodiments, the physiological parameters may include physical dimensions, such as size, position, and/or shape. For example, as shown in FIG. 3A, the physiological parameters for cardiac ultrasound imaging data of the heart in image 300 may include the height, width, or length of a chamber or valve, and/or the thickness of a cardiac wall. In the illustrated example, the physiological parameters of the heart in image 300 may include the height (A) and width (B) of a first heart chamber (e.g., corresponding to the left ventricle 302 shown in FIG. 3B discussed further below), the height (D) and width (C) of a second heart chamber (e.g., corresponding to the right ventricle 304 shown in FIG. 3B) and the width (E) of a heart wall. It is to be understood that height may include height of both the left ventricle 302 and the left atrium 306 (e.g., as shown in FIG. 3B), and height may include height of both right ventricle 304 and right atrium 308 (e.g., as shown in FIG. 3B). Additionally or alternatively, heart wall/cardiac wall thickness may also include other areas, including as shown at F, which comprises a plurality of layers: endocardium, myocardium, epicardium, pericardial cavity, parietal layer of serous pericardium, and fibrous pericardium. FIG. 3B generally illustrates three-dimensional model 310 which may be created and displayed using the method and system of the invention, more specifically, by employing AI model 706 to identify one or more physiological parameters A, B, C D, E and F, by selecting one or more model parameters and then by modifying those model parameters to match one or more of A, B, C D, E and F, thereby creating a photo-realistic 3D model (for example 310) with modified model parameters (e.g., one or more of A, B, C D, E and F).

In some embodiments, the physiological parameters can include the presence (or absence) of one or more features. For example, as shown in FIGS. 4A and 5A, the physiological parameters for lung ultrasound imaging data (shown as imaging data 400 and 500 respectively) may include the presence (or absence) of B line imaging artifacts. In the example illustrated in FIG. 4A, the physiological parameters in lung ultrasound imaging data 400 include the absence of any B lines. In contrast, in the example illustrated in FIG. 5A, the physiological parameters for lung ultrasound imaging data (shown as imaging data 500) include the presence of five B lines, shown as 510.

In some embodiments, one or more physiological parameters can be determined based on medical imaging data corresponding to more than one image or frame. For example, continuing with the example shown in FIG. 3A, the physiological parameters for cardiac ultrasound imaging data may include a heart rate that is determined from changes in physical dimensions across a set of images. For example, the heart rate may be determined from changes to one or more of the parameters A-F in a series of images taken over a period of time.

In some embodiments, the physiological parameters can be identified from processed imaging data, such as pre-scan converted data and/or post-scan converted data. In other embodiments, the physiological parameters can be identified from raw or unprocessed data that cannot be directly displayed as an image, such as RF data. In these latter embodiments where the AI model is trained to determine physiological parameters from raw or unprocessed data, the medical imaging system 100 may operate without actually generating viewable images from the raw or unprocessed data. This may allow the system 100 to operate more efficiently by reducing the computational load and/or processing power needed to process the raw/unprocessed data into viewable images. In turn, this may allow an ultrasound scanner that is a medical imaging device 102 to have fewer components, so that such an ultrasound scanner may be configured to be in a smaller form factor.

Referring back to FIG. 2, at act 240, the medical imaging system 100 can identify at least one model parameter of a selected three-dimensional model corresponding to the at least one physiological parameter. The three-dimensional model may be a visual representation of an anatomy that can be generated by the medical imaging system 100.

Figure 4B:
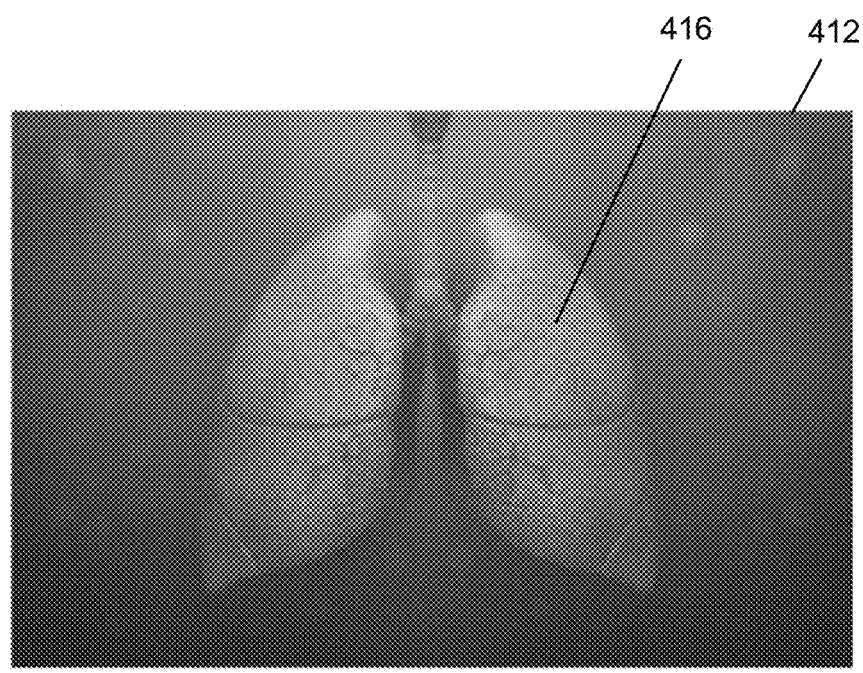
FIG. 4B is another example model that can be generated by the medical imaging system shown in FIG. 1, in accordance with at least one embodiment of the present invention.
Figure 5B:
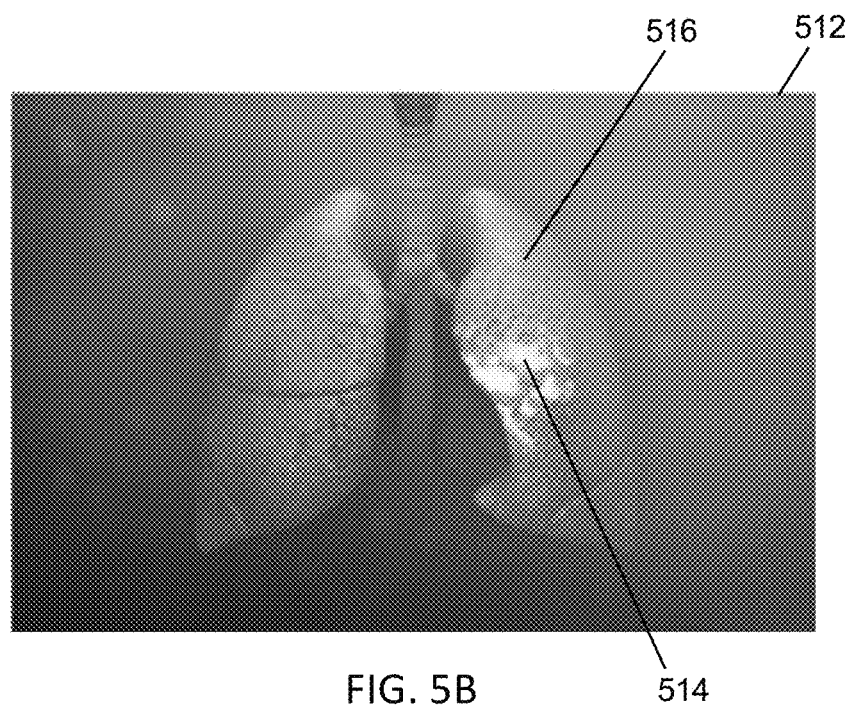
FIG. 5B is another example model that can be generated by the medical imaging system shown in FIG. 1, in accordance with at least one embodiment of the present invention.

FIGS. 3B, 4B, and 5B show example three-dimensional models. In particular, FIG. 3B shows an example model of a heart and FIGS. 4B and 5B show example models of lungs. Each model can be defined by one or more model parameters that control various aspects of the visual appearance of the model. These may be created and displayed using the method and system of the invention, more specifically, by employing AI model 706 to identify one or more physiological parameters (e.g., A, B, C D, E and F in FIG. 3A or the presence or absence of B-lines 510 in FIGS. 4 and 5), by selecting one or more model parameters and then by modifying those model parameters to match one or more physiological parameters, thereby creating a photo-realistic 3D model (for example 310, 412 and 512 shown in FIGS. 3B, 4B, and 5B respectively) with modified model parameters.

In some embodiments, the model parameters can define the size, position, or shape of one or more portions of the three-dimensional model. For example, as described above, the three-dimensional model shown in FIG. 3B is defined by model parameters A-F, which dictate the height, length, width and/or thickness of various portions of the 3D model. More specifically, model parameters A and B define the height and width of a first heart chamber, C and D define the height and width of a second heart chamber, and E an F define the width of a heart wall at two locations.

In some embodiments, the model parameters can define the colour or texture of one or more portions of the three-dimensional model. For example, the three-dimensional model shown in FIG. 4B (at 412) and 5B (at 512) are defined by a model parameter that dictates the level of tissue inflammation shown. For example, FIG. 4B illustrates model 412 of lungs with no inflammation, and FIG. 5B illustrates model 512 of lungs with inflammation 514 (e.g., the texture in right side 516 of the lungs shown in FIG. 5B is shown as having different brighter appearance at 514 than the texture in right side 416 of the lung shown in FIG. 4B).

Each model parameter can correspond to at least one physiological parameter determined from medical imaging data. For example, each of the size parameters A-F of the model shown in FIG. 3B can correspond to the physiological parameters A-F shown in FIG. 3A. Similarly, the inflammation level shown in FIGS. 4B and 5B can correspond to the number of B lines shown in FIGS. 4A and 5A respectively. The medical imaging system 100 can map each identified physiological parameter (e.g., identified from act 238 in FIG. 2) to one or more model parameters.

Referring still to FIG. 2, at 242, the medical imaging system 100, employing, for example, a rendering engine, can modify the three-dimensional model based on the at least one physiological parameter determined from the medical imaging data, so that the at least one model parameter reflects the at least one physiological parameter. For example, the medical imaging system 100 can adjust the model parameters to more closely represent the physiological parameters determined from the medical imaging data, thereby customizing the 3D model.

For example, continuing with the example shown in FIGS. 3A and 3B, the medical imaging system 100 can manipulate and morph the appearance of each of model parameters A-F in the model in FIG. 3B to respectively correspond to the size of each of physiological parameter A-F in the medical imaging data shown in FIG. 3A. Similarly, in the example shown in FIGS. 4A, 4B, 5A, and 5B, the medical imaging system 100 can adjust each the texture of the model shown in FIGS. 4B and 5B to reflect the number of B lines identified in the medical imaging data in FIGS. 4A and 5A respectively. For example, in FIG. 4B, the medical imaging system 100 can select a non-inflamed texture to represent the absence of B lines in the medical imaging data. In contrast, in FIG. 5B, the medical imaging system 100 can a select an inflamed texture to represent the presence of five B lines in the medical imaging data.

In various embodiments, the three-dimensional model may be pre-generated with predetermined or default model parameters. For example, the three-dimensional model can be generated prior to the acquisition of medical imaging data at act 232 of FIG. 2. The pre-generated models can then be modified by the medical imaging system 100 at act 242 of FIG. 2 based on the identified physiological parameters identified at act 238 of FIG. 2.

Referring back to FIG. 2, at 244, the medical imaging system 100 can display the modified model. For example, the modified three-dimensional model can be displayed on the computing device 110 or the medical imaging device 102.

In some embodiments, when displaying the 3D model, the 3D model can be selected and/or sliced and/or orientated to reflect the characteristics of the medical imaging data predicted by the AI model. For example, the AI model 706 may predict that certain medical imaging data corresponds to a 4-chamber apical cardiac view. When displaying the 3D model of the heart, the 3D model may then be sliced and orientated to show the 4-chamber apical cardiac view (e.g., as is shown in FIG. 3B), as part of act 244 in FIG. 2.

The displayed model may allow patients and/or medical professionals to visualize the physiological parameters with respect to the underlying anatomy, without displaying the corresponding medical imaging data. For example, the model shown in FIG. 3B can provide a visual depiction of the size of various parts of the heart, without displaying the ultrasound image of the heart shown in FIG. 3A. Similarly, the model shown in FIGS. 4B and 5B can provide a visual depiction of the inflammation of the lungs, without displaying the ultrasound image of the lungs in FIGS. 4A and 5A respectively. This may reduce the amount of processing power required by the medical imaging system 100 to process, render, and display the medical imaging data, which as noted, in some cases, may be in a raw format that is unsuitable for native display.

The displayed model may also be more easily understood by patients, and in some cases, medical professionals, as compared to the corresponding medical imaging data. For example, it may be difficult for a patient to understand the image plane or orientation of the cardiac ultrasound image shown in FIG. 3A. However, the patient may have an easier time visualizing the three-dimensional model shown in FIG. 3B. Likewise, the presence or absence of imaging artifacts in the lung ultrasound images shown in FIGS. 4A and 5A may be difficult for a patient to understand. However, the patient may more readily understand an illustrated texture indicating the degree of inflammation shown in FIGS. 4B and 5B.

It should be noted that, in various embodiments, the displayed model is not a complete and accurate representation of the imaged anatomy. Instead, only specific aspects of the model are representative of the medical imaging data. For example, in the example shown in FIG. 3B, various portions of the heart that are not defined by model parameters A-F may have dimensions that do not correspond to the actual heart imaged in FIG. 3A. Likewise, in the example shown in FIGS. 4B and 5B, the size of the lung may be different from that of the actual lung imaged in FIGS. 4A and 5A. Accordingly, the medical imaging system 100 may require less processing capacity, as compared to systems that generate more rigorous models (e.g., systems that uses 2D slices to generate 3D realistic volumes of the underlying imaged anatomy).

Referring again to FIG. 2, in various embodiments, subsequent to 244, acts 232 to 244 may be executed once again. This is optional and shown in FIG. 2 as a dotted line from act 244 back to act 232. For example, acts 232 to 244 can be repeated, iterated, or executed more than once. In some embodiments, the method 230 can be executed in substantially real-time so that a three-dimensional model is displayed and updated to reflect the live acquisition of medical imaging data. For example, continuing with the example shown in FIG. 3B, the model parameters A-D of the 3D model can be displayed and updated to show the deformation of the heart chambers during heartbeats.

Additionally or alternatively, in some cases, the acts in FIG. 2 can be performed once to provide a snapshot of the given physiological parameters at a point in time. The snapshot may be repeated over a number of scans, and the parameters from each snapshot may be averaged from the given session to obtain a more accurate assessment of the physiological parameters being measured. Such assessment may then be obtained over a longer period of time (e.g., a measurement taken once a week over a year) to monitor the physiological parameters that is reflective of a chronic underlying medical condition. For example, this may be useful for monitoring cardiac output, liver stiffness, and/or lung inflammation levels. In this manner, a patient may be able to use the present embodiments to visualize their progress over time.

The example embodiments discussed above have generally related to modifying elements of a 3D model. However, in some embodiments, analogous acts may additionally or alternatively be performed on a two-dimensional (2D) model or illustration. In such embodiments, in FIG. 2, act 240 may involve identifying at least one model parameter of a 2D model corresponding to the at least one physiological parameter identified from medical imaging data; act 242 may involve modifying the 2D model based on the at least one physiological parameter so that the at least one model parameter reflects the at least one physiological parameter; and act 244 may involve displaying the 2D model. The way in which these acts may be performed may generally otherwise be analogous to that described above for 3D models.

In an example, the 2D model may be a perspective view of an organ that is commonly understood to represent that organ. For example, in the example models discussed above in FIGS. 4B and 5B for lungs, it may be possible to display these models as 2D model representations that generally show the frontal or coronal plane of the lungs. Even on a 2D model, the texture on the lung may be changed to appear differently (e.g., increase in brightness or density) to reflect the number of B lines detected (which in turn reflects the amount of inflammation in the lungs).

Referring again to FIG. 6, shown there is an anatomical diagram illustrating a protocol for example locations that can be imaged by the medical imaging system shown in FIG. 1, in accordance with an embodiment of the present invention where the medical imaging device 102 is an ultrasound scanner. As noted above, scanning different locations may result in the determining of different physiological parameters. As illustrated, there are 4 locations on the front of the body, 4 locations on the back of the body, and 2 locations on the right side of the body which, if repeated on the left side of the body, would provide another 2 locations. Altogether, this provides for a total of 12 locations. In an example embodiment, if ultrasound imaging data were obtained from all such locations, a full screening of organs for which 3D models may be displayed may be obtained. For example, the full screening may include acquiring medical imaging data with physiological parameters that have correspondence to model parameters in 3D models of the heart, lungs, kidney, liver, gall bladder, muscles, bladder, uterus, foetus, other organs and/or anatomical structures.

It will be understood that the protocol shown in FIG. 6 is an example only. In another example embodiment, there may be 2 locations on the front of the body, 2 locations on the back of the body, and 1 location on each side of the body, and such a protocol may still be able to provide a full examination (e.g., if fewer views of certain organs were obtained and/or of fewer 3D models of organs were included in the full screening). Additionally, or alternatively, there may be screenings that are provided for a specific clinical application. For example, such a protocol may include scanning locations for obtaining medical imaging data related to a specific organ.

Referring now to FIG. 7, there is shown generally is a schematic diagram of a training and deployment of an AI model 706 and operating medical imaging system 100 in accordance with at least one embodiment of the present invention. According to an embodiment of the present invention, method 700 may be used to train one or more AI models 706 using labeled medical imaging data. The trained AI models 706 can then be used by the medical imaging system 100 (as shown in FIG. 1) to identify physiological parameters from new, unlabeled medical imaging data (e.g., in act 238 of method 230 of FIG. 2). In some embodiments, the trained AI models 706 may be used to identify physiological parameters which include but are not limited to: particular cross-sections or views of tissue/organs represented on the medical imaging data, particular sizes of tissue/organs represented on the medical imaging data, the orientations of the tissue/organs represented on the medical imaging data, anomalies in tissue/organs represented on the medical imaging data, and/or types or classes of medical imaging data (e.g., the type or class of anatomy imaged in the medical imaging data). Specifically, during use and deployment, neural network 710 may identify one or more physiological parameters and subsequently employing these one or more identified physiological parameters to select a corresponding 3D model. The corresponding 3D model may then be altered to modify, manipulate, or morph one or more model parameters within the corresponding 3D model to match the at least one identified physiological parameter, thereby customizing the visual appearance of the corresponding 3D model to formi a customized 3D model. In this context, customized refers to the alignment of the model parameters to the one or more identified physiological parameters.

In the diagram 700, the process can begin by receiving a set of training data at 702 and 703. The training data can include a set of medical imaging data which has been labeled in some manner. For example, the labeled medical imaging data may include imaging data in which one or more physiological parameters have been identified. In various embodiments, the labeled medical imaging data may include labeled ultrasound imaging data (e.g., one or more of RF data, pre-scan converted data, and/or post-scan converted). In the illustrated example, the labeled medical imaging data may include ultrasound images in which the size or other feature characteristics of a particular feature has been identified. In other embodiments, the labeled medical imaging data may include a set of medical imaging data in which the anatomy, cross-sectional view of the anatomy, and/or orientation and/or size characteristics of the anatomy has been identified. In various embodiments, the identification of the physiological features in the labeled medical imaging data may be performed by human medical experts. As described herein, these physiological features, which may be labelled for AI model training, are not to be limited herein at to the scope. In some embodiments, AI model 706 is trained with a robust selection of labelled medical imaging data, with varying views and orientations. For example, these different views may include coronal and/or transverse plane views of an anatomical feature, including views from different angles that combine any of a sagittal plane view, a coronal plane view, or a transverse plane view. These various views may train the AI model 706 to recognize the physiological parameter most accurately when the same physiological parameter is presented in different views (e.g., in the various views discussed above in relation to FIG. 6).

Referring still to FIG. 7, where medical image data/training data is shown by way of example to be ultrasound frames acquired from an ultrasound scanner (e.g., such as shown in FIG. 10 at 131), training data 702 and 703 (interchangeably referred to as training ultrasound frames 702 and 703) may include ultrasound frames with one or more physiological parameters that are labelled and tagged as acceptable (702). This generally means the labels on such training frames 702 are representative of that specific physiological parameter and which is most visually appropriate and representative of that parameter. Training data/ultrasound frames 703 labelled and tagged as unacceptable generally mean that such frames 703 are unrepresentative of that specific physiological parameter.

Both the training ultrasound frames labeled as 'Acceptable' and 'Unacceptable', for each particular anatomical feature (in whole or in part), may themselves be used for training and/or reinforcing AI model 706. This is shown in FIG. 7 with tracking lines from both 702 and 703 to training algorithm step 704.

In some embodiments, an optional pre-processing act 701 may be performed on the training data/ultrasound frames 702 and 703 to facilitate improved performance and/or accuracy when both labelling and training the machine learning (ML) algorithm. For example, it may be possible to pre-process the training data/ultrasound images 702 and 703 through a high contrast filter to reduce the granularity of greyscale on such images.

Additionally, or alternatively, it may be possible to reduce scale of the training data/ultrasound frames 702 and 703 prior to labelling and providing the training data/ultrasound frames 702 and 703 to the training algorithm step 704. Reducing the scale of the training data/ultrasound frames 702 and 703 as a preprocessing step may reduce the amount of image data to be processed during the training act 704, and thus may reduce the corresponding computing resources required for the training act 704 and/or improve the speed of the training act 704.

Various additional or alternative pre-processing acts may be performed in act 701. For example, these acts may include data normalization to ensure that the various the training data/ultrasound frames 702 and 703 used for training have generally the same dimensions and parameters. In various embodiments, the pre-processing act 234 used on newly acquired medical imaging data in FIG. 2 may generally correspond to the pre-processing act(s) 701 performed in FIG. 7. Aligning the pre-processing act(s) performed in FIG. 2 with that used during training in FIG. 7 will generally improve performance of the AI model since it more closely aligns the newly acquired data on which the AI model is run, with the data used to train the AI model in FIG. 7.

Referring still to FIG. 7, the various training data/ultrasound frames 702 and 703 may, at act 704, be used to train a ML algorithm. For example, the various training data/ultrasound frames 702 and 703, may be inputted into deep neural network 710 that can learn how to identify at least one physiological parameter in new medical imaging data, from within all trained and stored images. For example, and as shown in further detail in FIG. 3A, the neural network may learn to detect physiological parameters within cardiac ultrasound imaging data which may include the height, width, or length of a chamber or valve, or the thickness of a wall.

The result of the training may be the AI model 706, which represents the mathematical values, weights and/or parameters learned by the deep neural network to identify at least one physiological parameter, the tissue/organ type, cross-sectional view, and/or orientation in new medical imaging data, from within all trained and stored images. The training act 704 may involve various additional acts (not shown) to generate a suitable AI model 706. For example, these various deep learning techniques such as regression, classification, feature extraction, and the like. Any generated AI models may be iteratively tested to ensure they are not overfitted and sufficiently generalized for creating the comparison and list of probabilities in accordance with method of the invention.

In some embodiments, using a cross-validation method on the training process would optimize neural network hyper-parameters to try to ensure that the neural network can sufficiently learn the distribution of all possible physiological parameters without overfitting to the training data.

In some embodiments, after finalizing the neural network architecture, the neural network may be trained on all of the data available in the training image files. In various embodiments, batch training may be used and each batch may consist of multiple images, thirty-two for example, wherein each example image may be gray-scale, preferably 128*128 pixels although 256*256 pixels and other scaled may be used, without any preprocessing applied to it.

In some embodiments, the deep neural network parameters may be optimized using the Adam optimizer with hyper-parameters as suggested by Kingma, D. P., Ba, J. L.: Adam: a Method for Stochastic Optimization, International Conference on Learning Representations 2015 pp. 1-15 (2015), the entire contents of which are incorporated herewith. The weight of the convolutional layers may be initialized randomly from a zero-mean Gaussian distribution. In some embodiments, the Keras™ deep learning library with TensorFlow™ backend may be used to train and test the models.

In some embodiments, during training, many steps may be taken to stabilize learning and prevent the model from over-fitting. Using the regularization method, e.g., adding a penalty term to the loss function, has made it possible to prevent the coefficients or weights from getting too large. Another method to tackle the over-fitting problem is dropout. Dropout layers limit the co-adaptation of the feature extracting blocks by removing some random units from the neurons in the previous layer of the neural network based on the probability parameter of the dropout layer. Moreover, this approach forces the neurons to follow overall behaviour. This implies that removing the units would result in a change in the neural network architecture in each training step. In other words, a dropout layer performs similar to adding random noise to hidden layers of the model. A dropout layer with the dropout probability of 0.5 may be used after the pooling layers.

Data augmentation is another approach to prevent overfitting and add more transitional invariance to the model. Therefore, in some embodiments, the training images may be augmented on-the-fly while training. In every mini-batch, each sample may be translated horizontally and vertically, rotated and/or zoomed, for example. The present invention is not intended to be limited to any one particular form of data augmentation, in training the AI model. As such, any mode of data augmentation which enhances the size and quality of the data set, and applies random transformations which do not change the appropriateness of the label assignments may be employed, including but not limited to image flipping, rotation, translations, zooming, skewing, and elastic deformations.

Referring still to FIG. 7, after training has been completed, the sets of parameters stored in the storage memory may represent a trained neural network of a plurality of physiological parameters (in whole and parts thereof, within anatomical contexts) to then predict and identify a particular physiological parameter in new medical imaging data as compared to all trained and images.

In order to assess the performance of AI model 706, the stored AI model parameter values can be retrieved any time to perform image assessment through applying an image to the neural networks (shown as 710) represented thereby. In some embodiments, the deep neural network may include various layers such as convolutional layers, pooling layers, and fully connected layers. In some embodiments where the AI model 706 is trained and run on scan-converted ultrasound image data in (as opposed to RF or pre-scan converted ultrasound data), the final layers may include a softmax layer as an output layer having outputs which eventually would demonstrate respective determinations that an input set of pixels fall within a particular area for a physiological parameter (or part thereof) boundary. Accordingly, in some embodiments, the neural network may take at least one image as an input and output a binary mask indicating which pixels belong to the area for a physiological parameter (or part thereof) boundary (e.g., the AI model classifies which area each pixel belongs to).

More specifically, training images 702 and 703 may be labeled with one or more features associated with/are hallmarks of a physiological parameter (in whole or part) or representative of an adjacent identifying feature. This may include identifying a variety of features visualized in the captured training image. In at least some embodiments, this data may be received from trainer/user input. For example, a trainer/user may label the features relevant for the application visualized in each training image.

The image labeling can be performed, for example, by a trainer/user observing the training ultrasound images, via a display screen of a computing device, and manually annotating the image via a user interface. In some aspects, the training ultrasound images used for the method herein will only be images in which the image quality is of a sufficient quality threshold to allow for proper and accurate physiological parameter identification. In various embodiments, the training medical images can have different degrees of images brightness, speckle measurement and SNR.

Overall, the scope of the invention and accorded claims are not intended to be limited to any one particular process of training AI model 706. Such examples are provided herein by way of example only. AI model 706 may be trained by both supervised and unsupervised learning approaches although due to scalability, unsupervised learning approaches, which are well known in the art, are preferred. Other approaches may be employed to strengthen AI model 706.

In some embodiments where the training data includes medical imaging data of the heart, the training data may include the labeled data corresponding to typical cardiac views and orientations of the heart as may be acquired from one or more protocol positions indicated in FIG. 6. For example, the cardiac views may include a 4-chamber apical cardiac view and/or a 2-chamber parasternal cardiac view. If this labeled medical imaging data is included in the training data, the trained AI model may be able to recognize when medical imaging data corresponding to a similar view is obtained in new data (e.g., when new medical imaging data corresponding to a similar 4-chamber cardiac view is acquired as is shown in FIG. 3A). The AI model being able to recognize such anatomy type and/or cross-sectional view and/or orientation may allow an accurate cross-sectional view and orientation of the organ to be displayed (e.g., as discussed above at act 244 of FIG. 2).

Similarly, in another example where the training data includes ultrasound imaging data of the lungs, the labeled data may correspond to typical lung views and orientation as may be acquired from one or more protocol positions indicated in FIG. 6. As noted above, a typical lung view may have the presence or absence of B lines. If the AI model is trained to recognize when medical imaging data corresponding to a similar view is obtained in new data (e.g., as is shown above in FIG. 4A or 5A), the AI model may be able to recognize such anatomy type, so as to allow an accurate view of the lungs to be displayed (e.g., in act 244 of FIG. 2).

In various embodiments, the labeled medical imaging data may be generated based on manual user inputs. For example, in an example where labeling can be performed using the imaging app 112, the imaging application 112 (as shown in FIG. 1) may be configured to track where one or more physiological parameters are manually identified by an operator. For instance, in the example shown in FIG. 3A, the imaging application 112 may track the where the user labeled each of the cardiac size parameters A-F on the ultrasound image. Similarly, in the example in FIGS. 4A and 5A, the imaging application 112 may track the presence and/or number of B lines identified by the user. In some embodiments, the labeling input may additionally or alternatively be received on the server 122 which provides a labeling service and/or user interface (e.g., a web or online interface) for receiving such labeling input.

In some embodiments, the training data may include raw or unprocessed imaging data (e.g., RF data), and not include processed imaging data (e.g., pre-scan converted data and/or post-scan converted ultrasound images). For example, the medical imaging system 100 may collect user inputs based on the pre-scan converted data and/or post-scan converted data and correlate those inputs back to the RF data. The RF data can then be used as the training data instead of the pre-scan converted data and/or post-scan converted data.

As discussed herein, using the RF data as training data in this manner may allow RF data to be used as input to the neural network 710 so that predictions for the physiological parameters can be determined from RF data alone (as was labeled on the underlying pre-scan converted and/or post-scan converted images) without having to process the RF data into viewable ultrasound images.

Referring back to FIG. 7, as noted, at 704, the labeled medical imaging data can be used for training a machine learning (ML) algorithm. For example, as noted, the various training data may be inputted into a deep neural network that can learn how to correctly identify one or more physiological parameters from new medical imaging data. The neural network may alternatively or additionally identify the view and/or type of medical imaging data (e.g., the type of anatomy imaged in the medical imaging data).

For example, in some embodiments, once the training medical imaging data is obtained with tracked input for the physiological parameters, a deep neural network may use them as inputs. The associated expert details of the physiological parameters as desired may then be outputted to determine value sets of neural network parameters defining the neural networks.

Referring still to FIG. 7, after training has been completed, the sets of parameters stored in the storage memory may represent a trained neural network for identifying: the physiological parameters, the type data (e.g., which organ or anatomy is imaged in the medical imaging data), the cross-sectional view, and/or the orientation of new medical imaging data.

In order to assess the performance of the AI model, the stored AI model parameter values can be retrieved any time to perform image assessment through applying an image to the neural networks represented thereby.

In an example embodiment where the training data contains ultrasound images and ultrasound images are then generated to determine the physiological parameters discussed above in relation to FIG. 2 (as opposed to embodiments where training and prediction are performed only on non-image data such as RF data), the final layers may include a softmax layer as an output layer which has outputs that would demonstrate respective determinations that an input set of pixels correspond to a particular physiological parameter. Accordingly, in some embodiments, the neural network may take at least one image as an input and output a binary mask indicating which pixels correspond to a given physiological parameter (e.g., in the example of FIG. 3A, the AI model may classify the pixels corresponding to measurements A-F as belonging to cardiac parameters in the cardiac ultrasound image).

Referring still to FIG. 7, once a satisfactory AI model 706 is generated, the AI model 706 may be deployed for execution on a neural network 710 to predict physiological parameters and/or determine image type (e.g., the type of anatomy imaged in the medical imaging data) and/or the cross section of the organ represented on the medical imaging data and/or the orientation of the organ, on new medical imaging data 708. Notably, the neural network 710 is shown in FIG. 7 for illustration as a convolution neural network—which, as discussed above, may have various nodes in the input layer, hidden layers, and output layers. However, in various embodiments, different arrangements of the neural network 710 may be possible.

In various embodiments, the new medical imaging data 708 may be live images acquired by the medical imaging system 100. For example, the AI model 706 may be deployed for execution on the computing device 110 or the medical imaging device 102 (as shown in FIG. 1). In example embodiments where the medical imaging device 102 is an ultrasound scanner, the medical imaging data 708 may be live ultrasound images being acquired by the ultrasound scanner, or ultrasound images that have been stored at server 122. Such stored images are referenced as 709 in FIG. 7.

When executed in this manner, the AI model 706 may allow the neural network 710 to predict the type of image and/or particular physiological parameters from new medical imaging data 708 or stored images 709), resulting in corresponding medical imaging data 712 with predicted physiological parameters. The predicted physiological parameters may then be used to render three-dimensional models, as described further hereinbelow. As illustrated in FIG. 7, a measurement 'A' is shown as being predicted on image 712 that is analogous to the measurement 'A' that training data 702/703 was labeled with.

As noted above, in some embodiments, the training data 702 and 703 used to train the ML algorithm may have included just RF data that correlated to viewable ultrasound images on which physiological parameters were labeled. If this was the case, the input medical image data 708 (or 709) into the neural network 710 may also just be RF data. Since the neural network 710 was trained to predict physiological parameters from the RF data alone, only the RF data maybe needed as input 708 for the predicted physiological parameter. Configuring the AI model to operate on just RF data may reduce the computational resources needed to identify physiological parameters, as the resources for processing the RF data into viewable ultrasound images may be omitted. This may allow a hardware device executing the neural network 710 to be smaller and/or less costly to build.

Referring still to FIG. 7, in some embodiments, the medical imaging data 712 with predicted physiological parameters may optionally themselves be used for training and/or reinforcing the AI model 706. This is shown in FIG. 7 with a dotted line from the medical imaging data 712 with the predicted physiological parameter being provided to the training act 704. For example, the transmission of such reinforcement training ultrasound data may be sent to the server 122 which collects various predicted physiological parameters for updating the AI model 706.

FIG. 8 is flowchart diagram of the steps for training the AI model of FIG. 7 (e.g., act 704 of FIG. 7), according to an embodiment of the present invention. Method 800 is described below with regard to the systems and components depicted in FIGS. 10 and 11, though it should be appreciated that method 800 may be implemented with other systems and components without departing from the scope of the present disclosure in particular wherein the medical imaging device is other than an ultrasound scanner. In some embodiments, method 800 may be implemented as executable instructions in any appropriate combination of the imaging system 130 (as shown in FIG. 10), for example, an external computing device connected to the imaging system 130, in communication with the imaging system 130, and so on. As one example, method 800 may be implemented in non-transitory memory of a computing device, such as the controller (e.g., processor) of the imaging system 130 in FIG. 10. At 810, method 800 may include acquiring a dataset of sample images for training the neural network. Each sample image in the dataset may be a sample ultrasound image depicting a physiological parameter (in whole or part, or anatomical components thereof to adjacent thereto).

Referring still to FIG. 8, in step 810, a training ultrasound image may be obtained. For example, a training ultrasound image may be acquired by the scanner 131 (as shown in FIG. 10) transmitting and receiving ultrasound energy. The training ultrasound image may generally be a post-scan converted ultrasound image, although as described herein, other data types may be used, including RF data. While the method of FIG. 8 is described in relation to a single training ultrasound image, the method may also apply to the use of multiple training ultrasound images. While the method of FIG. 8 is described in relation to a post-scan ultrasound image, it is to be understood that pre-scan images, may be used, as described in U.S. patent application Ser. No. 17/187,851 filed Feb. 28, 2021, the entire contents of which are incorporated herein by reference.

Optionally, in step 812 (as shown in dotted outline), the resolution of the training ultrasound image may be adjusted. For example, the resolution may be increased or decreased. The purpose of this may be to provide the labeler (e.g., a medical professional with relevant clinical expertise) with training ultrasound images that have a more standardized appearance. This may help to maintain a higher consistency with which the labeler identifies anatomical features in the training ultrasound images. Besides the resolution, other parameters of the training ultrasound image may also be adjusted such as input scaling, screen size, pixel size, aspect ratio, and the removal of dead space, as described above (including, for example, data augmentation and other pre-processing steps).

In step 814, the training ultrasound image may be displayed on a display device, such as the display device 150 discussed in more detail below in relation to FIG. 10. The labeler can then identify a particular physiological parameter in the training ultrasound image by, for example, tagging it with a name from a pull-down menu or by using other labeling techniques and modalities. The labeler then can mark the training ultrasound image around the particular physiological parameter that the labeler has identified in the training ultrasound image. In step 814, the system that is used for the training may receive the identification of the physiological parameter. In step 816, the system may generate, from the labeler's marking inputs, a labeled training ultrasound image, and display it on the display device. In various embodiments, steps 814 and 816 may readily be interchanged with each other. The generation of labeled confirmation at step 816 may automatically proceed, without trainer intervention, using know anatomical measurement data which directs to the identity of a particular physiological parameter.

Once the training ultrasound image has been marked and labeled, the system may then remove, in step 818, optionally, (as shown in dotted outline), regions of the labeled ultrasound data frame that are both outside the area of the identified physiological parameter and outside areas relevant for the AI model to recognize the particular physiological parameter. For example, the labeled ultrasound data frame may be truncated at one or more sides. Truncation of some of the ultrasound data may allow the training of the AI model to proceed more quickly. At step 820, there is provided a redirection to complete steps 810 to 818 a plurality of times thereby to build a robust AI model, populated with images which are representative of specific physiological parameters which are most useful in clinical applications and for which the subsequent creation of 3D model renderings would be most assistive for patient visualization. At step 822, the labeled raw ultrasound data frame is then used for training the AI model 706 (e.g., as shown in FIG. 7). At step 824, once training is completed, the AI model may be used to perform identifications and selections on an unseen dataset to validate its performance, such evaluation at step 824 feeding data back to train the AI model at step 822.

Figure 9:
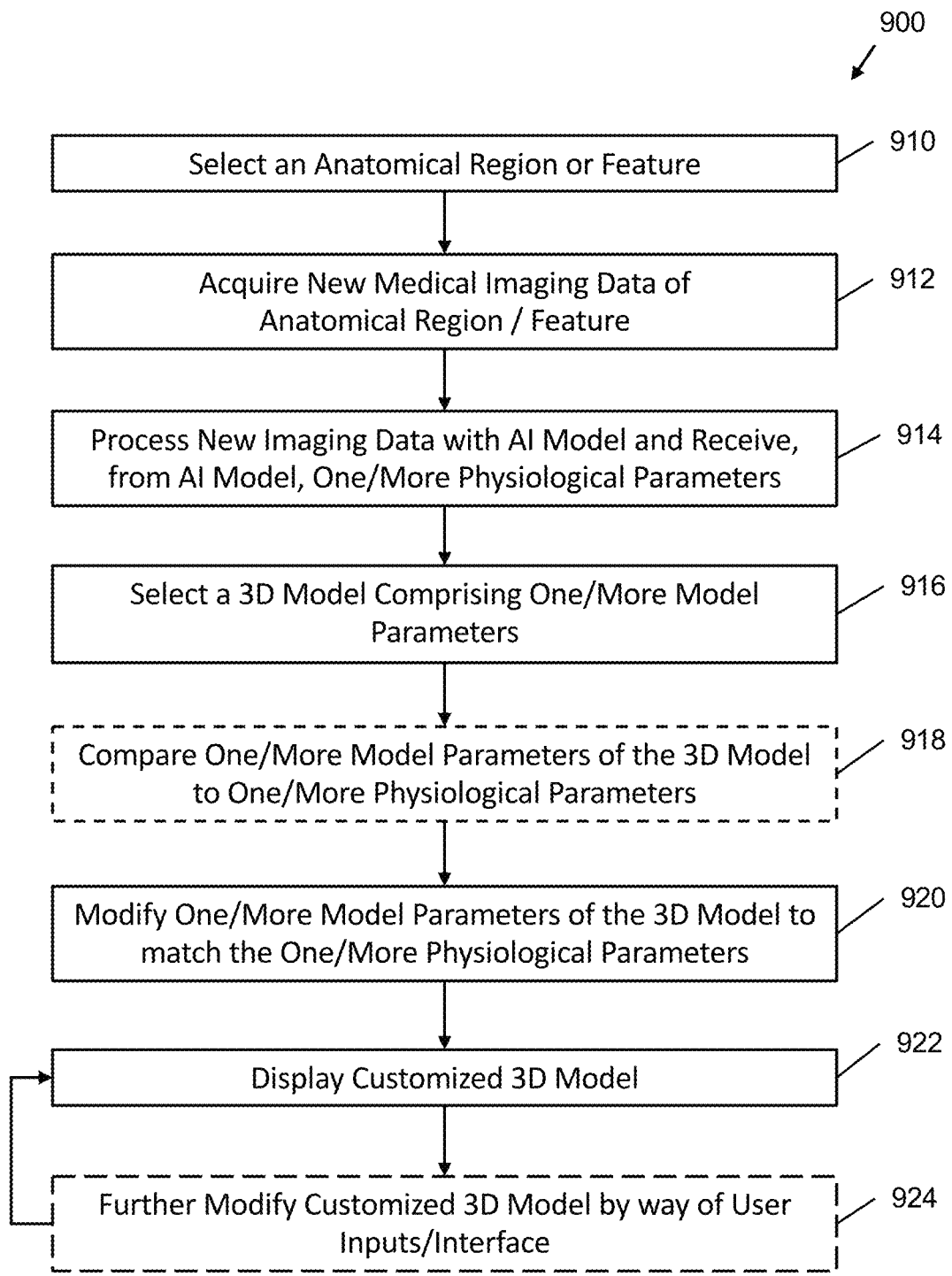
FIG. 9 is a representation of the steps for 3D model construction employing an imaging app and rendering engine, in accordance with at least one embodiment of the present invention.

FIG. 9 is a representation, shown as method 900, is a flowchart diagram illustrating the steps for customized 3D model construction employing, for example, the imaging app 112 shown in FIG. 1 and rendering engine, in accordance with at least one embodiment of the present invention. At 910, as a first general step, an anatomical region or anatomical feature is selected by a user. At act 912, new medical imaging data is acquired of the anatomical region/anatomical feature under investigation. This new medical imaging data acquired at act 912 is processed, at act 914 through a trained AI model and at least one physiological parameter is identified from the medical imaging data using an AI model. Then at act 916, the medical imaging system 100 can select and identify a 3D model, having at least one model parameter, wherein the at least one model parameter corresponds to the at least one physiological parameter. At an optional act 918, further and more detailed comparison between the at least one physiological parameter and the at least one model parameter may occur. At act 920, through the imaging app and/or rendering engine one or more of the model parameters, of the selected 3D model, are modified to match the one or more physiological parameters (prior identified by the AI model). By way of this step, the model parameter(s), which may be generic, are morphed to align with at least some of the specific characteristics of the physiological parameter(s) to create a customized 3D model. The three-dimensional model may be a visual representation of an anatomy that can be generated by the medical imaging system 100. At act 922, the customized 3D model is displayed for a user. An optional act 924 provides that the customized 3D model is further modified by way of user inputs, for example through a user interface on the imaging app 112 (as shown in FIG. 1), such modifications to the 3D model being displayed at act 922 (as shown by the line connecting act 924 back to act 922).

As described in detail herein, the methods and systems of the present invention apply: i) a trained AI model to identify one or more physiological parameters; and ii) an Imaging App (shown as 112 in FIG. 1) and/or rendering engine enabled to select a 3D model with one or more model parameters (such selection being based upon the identified physiological parameter(s)) and to modify the one or more model parameters to match the physiological parameters(s). In this way, the Imaging App/rendering engine create a photo-realistic 3D model which is customized to the identified physiological parameter(s). The rendering engine, in one aspect takes a morphological approach to adapting the selected 3D model using tools to change such as, for example, colour, textures, orientation, sizes (length, width, height, depth), shapes, shading, contrast, brightness, exposure, and brilliance.

In some aspects of the invention, a 3D model is dynamically and concurrently created, in real time, with medical image acquisition. As such, a 3D model (comprising one or more model parameters) may comprise areas which are initially not defined as/connected to a particular physiological parameter by the AI model. In one embodiment, such areas may be assigned a grey scale colour, until, upon the processing of further medical images (ex; further ultrasound scanning), such areas are colourized as identified.

Referring to FIG. 10, an exemplary system 130 is shown for identifying one or more physiological parameters using an AI model and further employing the at least one identified physiological parameter to select a corresponding 3D model, and modifying the corresponding 3D model to alter one or more model parameters therein, to match the at least one identified physiological parameter, thereby customizing the visual appearance of the corresponding 3D model, forming a customized, rendered 3D model. It is to be understood that this is an exemplary system, which is ultrasound scanner based, and the substitution of other medical imaging devices is entirely within the scope of the invention.

The system 130 includes an ultrasound scanner 131 with a processor 132, which is connected to a non-transitory computer readable memory 134 storing computer readable instructions 136, which, when executed by the processor 132, may cause the scanner 131 to provide one or more of the functions of the system 130. Such functions may be, for example, the acquisition of ultrasound data, the processing of ultrasound data, the scan conversion of ultrasound data, the transmission of ultrasound data or ultrasound frames to a display device 150, the detection of operator inputs to the ultrasound scanner 131, and/or the switching of the settings of the ultrasound scanner 131.

Also stored in the computer readable memory 134 may be computer readable data 138, which may be used by the processor 132 in conjunction with the computer readable instructions 136 to provide the functions of the system 130. Computer readable data 138 may include, for example, configuration settings for the scanner 131, such as possible presents that instruct the processor 132 how to collect and process the ultrasound data for a plurality of different physiological parameters and how to acquire a series of ultrasound frames.

The scanner 131 may include an ultrasonic transducer 142 that transmits and receives ultrasound energy in order to acquire ultrasound frames.

The scanner 131 may include a communications module 140 connected to the processor 132. In the illustrated example, the communications module 140 may wirelessly transmit signals to and receive signals from the display device 150 along wireless communication link 144. The protocol used for communications between the scanner 131 and the display device 150 may be WiFi™ or Bluetooth™, for example, or any other suitable two-way radio communications protocol. In some embodiments, the scanner 131 may operate as a WiFi™ hotspot, for example. Communication link 144 may use any suitable wireless communications network connection. In some embodiments, the communication link between the scanner 131 and the display device 150 may be wired. For example, the scanner 131 may be attached to a cord that may be pluggable into a physical port of the display device 150.

In various embodiments, the display device 150 may be, for example, a laptop computer, a tablet computer, a desktop computer, a smart phone, a smart watch, spectacles with a built-in display, a television, a bespoke display or any other display device that is capable of being communicably connected to the scanner 131. The display device 150 may host a screen 152 and may include a processor 154, which may be connected to a non-transitory computer readable memory 156 storing computer readable instructions 158, which, when executed by the processor 154, cause the display device 150 to provide one or more of the functions of the system 130. Such functions may be, for example, the receiving of ultrasound data that may or may not be pre-processed; scan conversion of received ultrasound data into an ultrasound image; processing of ultrasound data in image data frames; the display of a user interface; the control of the scanner 131; the display of an ultrasound image on the screen 152; the processing of a identifying physiological parameters (against a trained AI model); operating the imaging app 112 (as described in regard to FIG. 1) and/or the storage, application, reinforcing and/or training of the AI model. The screen 152 may comprise a touch-sensitive display (e.g., touchscreen) that can detect a presence of a touch from the operator on screen 152 and can also identify a location of the touch in screen 152. The touch may be applied by, for example, at least one of an individual's hand, glove, stylus, or the like. As such, the touch-sensitive display may be used to manipulate the selected 3D model (and the model parameters) to customize such model parameters to match the physiological parameters. The screen 152 and/or any other user interface may also communicate audibly. The display device 150 is configured to present information to the operator during or after the imaging or data acquiring session. The information presented may include ultrasound images (e.g., one or more 2D frames), graphical elements, measurement graphics of the displayed images, user-selectable elements, user settings, and other information (e.g., administrative information, personal information of the patient, and the like).

Also stored in the computer readable memory 156 may be computer readable data 160, which may be used by the processor 154 in conjunction with the computer readable instructions 158 to provide the functions of the system 130. Computer readable data 160 may include, for example, settings for the scanner 131, such as presets for acquiring ultrasound data; settings for a user interface displayed on the screen 152; and/or data for one or more AI models, within the scope of the invention. Settings may also include any other data that is specific to the way that the scanner 131 operates or that the display device 150 operates.

It can therefore be understood that the computer readable instructions and data used for controlling the system 130 may be located either in the computer readable memory 134 of the scanner 131, the computer readable memory 156 of the display device 150, and/or both the computer readable memories 134, 156.

The display device 150 may also include a communications module 162 connected to the processor 154 for facilitating communication with the scanner 131. In the illustrated example, the communications module 162 wirelessly transmits signals to and receives signals from the scanner 131 on wireless communication link 144. However, as noted, in some embodiments, the connection between scanner 131 and display device 150 may be wired.

Referring to FIG. 11, a system 200 is shown in which there are multiple similar or different scanners 131, 202, 204 connected to their corresponding display devices 150, 206, 208 and either connected directly, or indirectly via the display devices, to a communications network 210, such as the internet. The scanners 131, 202, 204 may be connected onwards via the communications network 210 to a server 220.

The server 220 may include a processor 222, which may be connected to a non-transitory computer readable memory 224 storing computer readable instructions 226, which, when executed by the processor 222, cause the server 220 to provide one or more of the functions of the system 200. Such functions may be, for example, the receiving of ultrasound frames, the processing of ultrasound data in ultrasound frames, the control of the scanners 131, 202, 204, the processing of a physiological parameter identification (against the trained AI model), and/or machine learning activities related to one or more AI models, and the processing of data relating to the imaging app and/or rendering engine.

Also stored in the computer readable memory 224 may be computer readable data 228, which may be used by the processor 222 in conjunction with the computer readable instructions 226 to provide the functions of the system 200. Computer readable data 228 may include, for example, settings for the scanners 131, 202, 204 such as preset parameters for acquiring ultrasound data, settings for user interfaces displayed on the display devices 150, 206, 208, and data for one or more AI models. Settings may also include any other data that is specific to the way that the scanners 131, 202, 204 operate or that the display devices 150, 206, 208 operate.

It can therefore be understood that the computer readable instructions and data used for controlling the system 200 may be located either in the computer readable memory of the scanners 131, 202, 204, the computer readable memory of the display devices 150, 206, 208, the computer readable memory 224 of the server 220, or any combination of the foregoing locations.

As noted above, even though the scanners 131, 202, 204 may be different, each ultrasound frame acquired may be used by the AI model for training purposes. Likewise, the ultrasound frames acquired by the individual scanners 131, 202, 204 may all be processed against the AI model for reinforcement of the AI model.

In some embodiments, the AI model 706 present in the display devices 150, 206, 208 may be updated from time to time from an AI model 706 present in the server 220, where the AI model present in the server is continually trained using ultrasound frames of additional physiological parameters acquired by multiple scanners 131, 202, 204.

While a number of exemplary aspects and embodiments have been discussed above, those of skill in the art will recognize that may be certain modifications, permutations, additions, and sub-combinations thereof. While the above description contains many details of example embodiments, these should not be construed as essential limitations on the scope of any embodiment. Many other ramifications and variations are possible within the teachings of the various embodiments.

Interpretation of Terms

Unless the context clearly requires otherwise, throughout the description and the claims:
"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Unless the context clearly requires otherwise, throughout the description and the Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASIC s"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples but should be given the broadest interpretation consistent with the description as a whole.

Claim Support

The present invention provides, in one aspect, a method of creating a 3D model, which is a visual representation of at least one physiological parameter, the method comprising: deploying an AI model to execute on a computing device communicably connected to a medical imaging device, said medical imaging device acquiring medical imaging data, wherein the AI model is trained so that when it is deployed, the computing device identifies at least one physiological parameter from medical imaging data; acquiring, at the computing device, new medical imaging data; processing, using the AI model, the new medical imaging data to identify at least one physiological parameter (the "at least one identified physiological parameter"); employing the at least one identified physiological parameter to select a corresponding 3D model; modifying the corresponding 3D model to alter one or more model parameters therein, to match the at least one identified physiological parameter, thereby customizing the visual appearance of the corresponding 3D model.

Preferably, the medical imaging device is selected from group consisting of an ultrasound scanner, an x-ray imager, and a magnetic resonance imaging (MRI) imager. Preferably, the corresponding 3D model is a visual representation of one or more anatomical features. Preferably, the corresponding 3D model is pre-generated with predetermined or default model parameters. Preferably, the step of modifying the corresponding 3D model is achieved by a rendering engine which morphs and manipulates the model parameters. Preferably, the rendering engine is controlled by a user interface. Preferably, the model parameters are selected from the group consisting of the size, position, orientation, shape, colour, shading, contrast, and texture of one or more portions of the selected 3D model. Preferably, the medical imaging device is an ultrasound scanner, and the AI model is trained using medical image data selected from the group consisting of radio frequency (RF) data, pre-scan converted data, and post-scan converted data and wherein the medical imaging device is an ultrasound scanner, and the new medical imaging data selected from the group consisting of radio frequency (RF) data, pre-scan converted data, and post-scan converted data. Preferably, the user interface enables user input via at least one of the following modalities: a button, a touch-sensitive region of the user interface, a dial, a slider, a drag gesture, a voice command, a keyboard, a mouse, a trackpad, a touchpad, or any combination thereof. Preferably, the physiological parameter is selected from the group consisting of one or more physical dimensions of an anatomical feature, a presence or absence of an anatomical feature, in whole or part, and one or more anomalies in an anatomical feature. Preferably, the selected 3D model is dynamically and concurrently created, in real time, with medical imaging data acquisition and the selected 3D model (comprising one or more model parameters) comprises one or more areas which are not initially matched to a physiological parameter and wherein the areas are assigned a grey scale colour, until, upon processing of additional medical imaging data, the areas are colourized, as identified.

In another aspect, the present invention provides a system for creating a 3D model, which is a visual representation of at least one physiological parameter, said system comprising: a medical imaging device configured to acquire new medical imaging data; a computer processor that is communicatively connected to the medical imaging device and configured to: process the new medical imaging data against an artificial intelligence ("AI") model, wherein said AI model is trained so that when it is deployed, the computer processor identifies at least one physiological parameter from medical imaging data; process, using the AI model, the new medical imaging data to identify at least one physiological parameter (the "at least one identified physiological parameter"); employ the at least one identified physiological parameter to select a corresponding 3D model; modify the corresponding 3D model to alter one or more model parameters therein, to match the at least one identified physiological parameter, thereby customizing the visual appearance of the corresponding 3D model, forming a customized 3D model; and a display device configured to display to a system user at least the customized 3D model.

Preferably, in this system, the medical imaging device is selected from group consisting of an ultrasound scanner, an x-ray imager, and a magnetic resonance imaging (MM) imager. Preferably, in this system the corresponding 3D model is a visual representation of one or more anatomical features. Preferably, in this system, the corresponding 3D model is pre-generated with predetermined or default model parameters. Preferably, in this system, there is provided a rendering engine which modifies the corresponding 3D model by morphing and manipulating the model parameters. Preferably, in this system, the rendering engine is controlled by a user interface. Preferably, in this system, the user interface enables user input via at least one of the following modalities: a button, a touch-sensitive region of the user interface, a dial, a slider, a drag gesture, a voice command, a keyboard, a mouse, a trackpad, a touchpad, or any combination thereof. Preferably, in this system, the physiological parameter is selected from the group consisting of one or more physical dimensions of an anatomical feature, a presence or absence of an anatomical feature, in whole or part, and one or more anomalies in an anatomical feature.

In yet another aspect of the invention, there is provided a computer-readable media storing computer-readable instructions, which, when executed by a processor cause the processor to: process new medical imaging data against an artificial intelligence ("AI") model, wherein said AI model is trained so that when it is deployed, the computer processor identifies at least one physiological parameter from the new medical imaging data (the "at least one identified physiological parameter"); employ the at least one identified physiological parameter to select a corresponding 3D model; modify the corresponding 3D model to alter one or more model parameters therein, to match the at least one identified physiological parameter, thereby customizing the visual appearance of the corresponding 3D model.

What is claimed is:

1. A method of creating a 3D model, which is a visual representation of at least one physiological parameter, the method comprising:
    deploying an artificial intelligence (AI) model to execute on a computing device communicably connected to an ultrasound scanner, said ultrasound scanner acquiring medical imagine data, wherein the AI model is trained using medical imaging data selected from the group consisting of radop frequency (RF) data, pre-scan converted data, and post-scan converted data so that when it is deployed, the computing device identifies at least one physiological parameter from medical imaging data;
    acquiring, at the computing device, new medical imaging data selected from the group consisting of RF data, pre-scan converted data, and post-scan converted data;
    processing, using the AI model, the new medical imaging data to identify at least one physiological parameter;
    employing the identified at least one physiological parameter to select a corresponding 3D model;
    modifying the corresponding 3D model to alter one or more model parameters therein, to match the identified at least one physiological parameter, thereby customizing the visual appearance of the corresponding 3D model.

2. The method of claim 1 wherein the corresponding 3D model is a visual representation of one or more anatomical features.

3. The method of claim 1 wherein the corresponding 3D model is pre-generated with predetermined or default model parameters.

4. The method of claim 1 wherein the step of modifying the corresponding 3D model is achieved by a rendering engine which morphs and manipulates the model parameters.

5. The method of claim 4 wherein the rendering engine is controlled by a user interface.

6. The method of claim 5 wherein the user interface enables user input via at least one of the following modalities: a button, a touch-sensitive region of the user interface, a dial, a slider, a drag gesture, a voice command, a keyboard, a mouse, a trackpad, a touchpad, or any combination thereof.

7. The method of claim 1 wherein the model parameters are selected from the group consisting of the size, position, orientation, shape, colour, shading, contrast, and texture of one or more portions of the selected 3D model.

8. The method of claim 1 wherein the physiological parameter is selected from the group consisting of one or more physical dimensions of an anatomical feature, a presence or absence of an anatomical feature, in whole or part, and one or more anomalies in an anatomical feature.

9. A system for creating a 3D model, which is a visual representation of at least one physiological parameter, said system comprising:
 an ultrasound scanner configured to acquire new medical imaging data selected from the group consisting of radio frequency (RF) data, pre-scan converted data, and post-scan converted data;
 a computer processor that is communicatively connected to the ultrasound scanner and configured to:
  process the new medical imaging data against an artificial intelligence ("AI") model, wherein said AI model is trained so that when it is deployed, the computer processor identifies at least one physiological parameter from medical imaging data;
  process, using the AI model, the new medical imaging data to identify at least one physiological parameter;
  employ the identified at least one physiological parameter to select a corresponding 3D model;
  modify the corresponding 3D model to alter one or more model parameters therein, to match the identified at least one physiological parameter, thereby customizing the visual appearance of the corresponding 3D model, forming a customized 3D model; and a display device configured to display to a system user at least one customized 3D model.

10. The system of claim 9 wherein the corresponding 3D model is a visual representation of one or more anatomical features.

11. The system of claim 9 wherein the corresponding 3D model is pre-generated with predetermined or default model parameters.

12. The system of claim 9 comprising a rendering engine which modifies the corresponding 3D model by morphing and manipulating the model parameters.

13. The system of claim 12 wherein the rendering engine is controlled by a user interface.

14. The system of claim 13 wherein the user interface enables user input via at least one of the following modalities: a button, a touch-sensitive region of the user interface, a dial, a slider, a drag gesture, a voice command, a keyboard, a mouse, a trackpad, a touchpad, or any combination thereof.

15. The system of claim 9 wherein the physiological parameter is selected from the group consisting of one or more physical dimensions of an anatomical feature, a presence or absence of an anatomical feature, in whole or part, and one or more anomalies in an anatomical feature.

16. A non-transitory computer-readable media storing computer-readable instructions, which, when executed by a processor cause the processor to:
 process new medical imaging data selected from the group consisting of radio frequency (RF) data, pre-scan converteddata, and post-scan converted data, acquired from an ultrasound scanner, against an artificial intelligence ("AI") model, wherein said AI model is trained so that when it is deployed, the computer processor identifies at least one physiological parameter from the new medical imaging data;
 employ the identified at least one physiological parameter to select a corresponding 3D model;
 modify the corresponding 3D model to alter one or more model parameters therein, to match the identified at least one physiological parameter, thereby customizing the visual appearance of the corresponding 3D model.

17. A method of creating a 3D model, which is a visual representation of at least one physiological parameter, the method comprising:
 deploying an artificial intelligence (AI) model to execute on a computing device communicably connected to a medical imaging device, said medical imaging device acquiring medical imaging data, wherein the AI model is trained so that when it is deployed, the computing device identifies at least one physiological parameter from medical imaging data;
 acquiring, at the computing device, new medical imaging data;
 processing, using the AI model, the new medical imaging data to identify at least one physiological parameter;
 employing the identified at least one identified physiological parameter to select a corresponding 3D model;
 modifying the corresponding 3D model, by a rendering engine which morphs and manipulates model parameters, to alter one or more model parameters therein, to match the identified at least one physiological parameter, thereby custominzing the visual appearance of the corresponding 3D model, wherein the 3D model is dynamically and concurrently created, in real time, with medical imaging data acquisition and the 3D model comprises one or more areas which are not initially matched to a physiological parameter and wherein the areas are assigned a grey scale colour, until, upon processing of additional medical imaging data, the areas are colourized, as identified.

18. The method of claim 17 wherein the corresponding 3D model is a visual representation of one or more anatomical features.

19. The method of claim 17 wherein the corresponding 3D model is pre-generated with predetermined or default model parameters.

20. The method of claim 17 wherein the physiological parameter is selected from the group consisting of one or more physical dimensions of an anatomical feature, a presence or absence of an anatomical feature, in whole or part, and one or more anomalies in an anatomical feature.

* * * * *

UNITED STATES PATENT AND TRADEMARK OFFICE
CERTIFICATE OF CORRECTION

| | |
|---|---|
| PATENT NO. | : 11,804,020 B2 |
| APPLICATION NO. | : 17/553541 |
| DATED | : October 31, 2023 |
| INVENTOR(S) | : Pelissier et al. |

It is certified that error appears in the above-identified patent and that said Letters Patent is hereby corrected as shown below:

In the Claims

In Claim 1, at Line 48, the term "radop" should be replaced with "radio"

Signed and Sealed this
Twelfth Day of December, 2023

Katherine Kelly Vidal
*Director of the United States Patent and Trademark Office*